(12) United States Patent
Ben Nun

(10) Patent No.: US 10,166,096 B2
(45) Date of Patent: Jan. 1, 2019

(54) FOLDABLE ACCOMMODATING INTRAOCULAR LENS

(71) Applicant: ForSight Vision6, Inc., Menlo Park, CA (US)

(72) Inventor: Joshua Ben Nun, D.N. Vitkin (IL)

(73) Assignee: ForSight Vision6, Inc., Menlo Park, CA (US)

(*) Notice: Subject to any disclaimer, the term of this patent is extended or adjusted under 35 U.S.C. 154(b) by 0 days.

(21) Appl. No.: 15/808,579

(22) Filed: Nov. 9, 2017

(65) Prior Publication Data

US 2018/0221138 A1 Aug. 9, 2018

Related U.S. Application Data

(63) Continuation of application No. 14/486,027, filed on Sep. 15, 2014, now Pat. No. 9,814,568, which is a continuation of application No. 13/604,172, filed on Sep. 5, 2012, now Pat. No. 8,834,565, which is a continuation of application No. 11/910,133, filed as application No. PCT/IL2006/000406 on Mar. 30, 2006, now abandoned.

(60) Provisional application No. 60/724,896, filed on Oct. 11, 2005, provisional application No. 60/672,081, filed on Apr. 18, 2005, provisional application No. 60/666,180, filed on Mar. 30, 2005.

(51) Int. Cl.
*A61F 2/16* (2006.01)

(52) U.S. Cl.
CPC .......... *A61F 2/1635* (2013.01); *A61F 2/1613* (2013.01); *A61F 2/1648* (2013.01); *A61F 2002/1683* (2013.01); *A61F 2210/0014* (2013.01)

(58) Field of Classification Search
CPC .... A61F 2/1613; A61F 2/1624; A61F 2/1629; A61F 2/1635; A61F 2/1648; A61F 2002/1682; A61F 2002/1689; A61F 2002/16902
See application file for complete search history.

(56) References Cited

U.S. PATENT DOCUMENTS

| 3,950,082 A | 4/1976 | Volk |
| 4,122,556 A | 10/1978 | Poler |
| 4,159,546 A | 7/1979 | Shearing |

(Continued)

FOREIGN PATENT DOCUMENTS

| CN | 101795642 A | 8/2010 |
| EP | 0 156 472 A1 | 10/1985 |

(Continued)

OTHER PUBLICATIONS

U.S. Appl. No. 14/067,839, filed Oct. 30, 2013, US 2014/0058507.

(Continued)

*Primary Examiner* — Howie Matthews
(74) *Attorney, Agent, or Firm* — Mintz Levin Cohn Ferris Glovsky and Popeo, P.C.

(57) ABSTRACT

Accommodating intraocular (AIOL) assemblies for enabling post implantation in situ manual selective displacement of an AIOL along a human eye's visual axis relative to stationary anchor points. Axial displacement may be over a continuous range or alternatively at discrete axial stopping positions typically from about 100 μm to about 300 μm apart. Novels AIOLs designed to be at least partially folded for facilitating insertion into a human eye through a relatively small incision.

10 Claims, 16 Drawing Sheets

(56) References Cited

U.S. PATENT DOCUMENTS

| | | |
|---|---|---|
| 4,254,509 A | 3/1981 | Tennant |
| 4,298,994 A | 11/1981 | Clayman |
| 4,340,979 A | 7/1982 | Kelman |
| 4,373,218 A | 2/1983 | Schachar |
| 4,409,690 A | 10/1983 | Gess |
| 4,409,691 A | 10/1983 | Levy |
| 4,445,998 A | 5/1984 | Kanda et al. |
| 4,446,581 A | 5/1984 | Blake |
| 4,494,254 A | 1/1985 | Lopez |
| 4,530,117 A | 7/1985 | Kelman |
| RE31,963 E | 8/1985 | Kelman |
| 4,556,998 A | 12/1985 | Siepser |
| 4,575,374 A | 3/1986 | Anis |
| 4,581,033 A | 4/1986 | Callahan |
| 4,589,147 A | 5/1986 | Nevyas |
| 4,591,358 A | 5/1986 | Kelman |
| 4,615,701 A | 10/1986 | Woods |
| 4,671,283 A | 6/1987 | Hoskin et al. |
| 4,676,794 A | 6/1987 | Kelman |
| 4,685,921 A | 8/1987 | Peyman |
| 4,731,078 A | 3/1988 | Stoy et al. |
| 4,734,095 A | 3/1988 | Siepser |
| 4,750,904 A | 6/1988 | Price, Jr. |
| 4,769,035 A | 9/1988 | Kelman |
| 4,782,820 A | 11/1988 | Woods |
| 4,787,903 A | 11/1988 | Grendahl |
| 4,808,181 A | 2/1989 | Kelman |
| 4,816,030 A | 3/1989 | Robinson |
| 4,816,031 A | 3/1989 | Pfoff |
| 4,842,601 A | 6/1989 | Smith |
| RE33,039 E | 8/1989 | Arnott |
| 4,865,601 A | 9/1989 | Caldwell et al. |
| 4,888,012 A | 12/1989 | Horn et al. |
| 4,892,543 A | 1/1990 | Turley |
| 4,932,966 A | 6/1990 | Christie et al. |
| 4,932,968 A | 6/1990 | Caldwell et al. |
| 4,957,505 A | 9/1990 | McDonald |
| 4,969,897 A | 11/1990 | Kalb |
| 4,976,732 A | 12/1990 | Vorosmarthy |
| 4,990,159 A | 2/1991 | Kraff |
| 5,026,373 A | 6/1991 | Ray et al. |
| 5,066,301 A | 11/1991 | Wiley |
| 5,078,742 A | 1/1992 | Dahan |
| 5,171,266 A | 12/1992 | Wiley et al. |
| 5,171,268 A | 12/1992 | Ting et al. |
| 5,176,701 A | 1/1993 | Dusek et al. |
| RE34,424 E | 10/1993 | Walman |
| 5,275,623 A | 1/1994 | Sarfarazi |
| 5,282,851 A | 2/1994 | Jacob-LaBarre |
| 5,288,293 A | 2/1994 | O'Donnell, Jr. |
| 5,336,262 A | 8/1994 | Chu |
| 5,346,502 A | 9/1994 | Estabrook et al. |
| 5,443,506 A | 8/1995 | Garabet |
| 5,476,512 A | 12/1995 | Sarfarazi |
| 5,476,514 A | 12/1995 | Cumming |
| 5,476,515 A | 12/1995 | Kelman et al. |
| 5,480,426 A | 1/1996 | Chu |
| 5,484,447 A | 1/1996 | Waldock et al. |
| 5,489,302 A | 2/1996 | Skottun |
| 5,496,366 A | 3/1996 | Cumming |
| 5,522,891 A | 6/1996 | Klaas |
| 5,567,365 A | 10/1996 | Weinschenk, III et al. |
| 5,571,177 A | 11/1996 | Deacon et al. |
| 5,584,304 A | 12/1996 | Brady |
| 5,607,472 A | 3/1997 | Thompson |
| 5,628,795 A | 5/1997 | Langerman |
| 5,674,282 A | 10/1997 | Cumming |
| 5,684,637 A | 11/1997 | Floyd |
| 5,722,952 A | 3/1998 | Schachar |
| 5,752,960 A | 5/1998 | Nallakrishnan |
| 5,766,244 A | 6/1998 | Binder |
| 5,766,245 A | 6/1998 | Fedorov et al. |
| 5,774,273 A | 6/1998 | Bornhorst |
| 5,800,806 A | 9/1998 | Yamamoto |
| 5,843,188 A | 12/1998 | McDonald |
| 5,871,455 A | 2/1999 | Ueno |
| 5,895,610 A | 4/1999 | Chang et al. |
| 5,919,230 A | 7/1999 | Sambursky |
| 5,932,205 A | 8/1999 | Wang et al. |
| 5,968,094 A | 10/1999 | Werblin et al. |
| 5,984,962 A | 11/1999 | Anello et al. |
| 6,007,579 A | 12/1999 | Lipshitz et al. |
| 6,013,101 A | 1/2000 | Israel |
| 6,027,531 A | 2/2000 | Tassignon |
| 6,051,024 A | 4/2000 | Cumming |
| 6,096,078 A | 8/2000 | McDonald |
| 6,110,202 A | 8/2000 | Barraquer et al. |
| 6,117,171 A | 9/2000 | Skottun |
| 6,120,538 A | 9/2000 | Rizzo, III et al. |
| 6,129,759 A | 10/2000 | Chambers |
| 6,143,315 A | 11/2000 | Wang et al. |
| 6,164,282 A | 12/2000 | Gwon et al. |
| 6,188,526 B1 | 2/2001 | Sasaya et al. |
| 6,193,750 B1 | 2/2001 | Cumming |
| 6,197,057 B1 | 3/2001 | Peyman et al. |
| 6,197,059 B1 | 3/2001 | Cumming |
| 6,200,342 B1 | 3/2001 | Tassignon |
| 6,228,115 B1 | 5/2001 | Hoffmann et al. |
| 6,261,321 B1 | 7/2001 | Kellan |
| 6,277,146 B1 | 8/2001 | Peyman et al. |
| 6,280,469 B1 | 8/2001 | Terry et al. |
| 6,280,471 B1 | 8/2001 | Peyman et al. |
| 6,299,618 B1 | 10/2001 | Sugiura |
| 6,299,641 B1 | 10/2001 | Woods |
| 6,342,073 B1 | 1/2002 | Cumming et al. |
| 6,387,126 B1 | 5/2002 | Cumming |
| 6,406,494 B1 | 6/2002 | Laguette et al. |
| 6,423,094 B1 | 7/2002 | Sarfarazi |
| 6,443,984 B1 | 9/2002 | Jahn et al. |
| 6,443,985 B1 | 9/2002 | Woods |
| 6,450,642 B1 | 9/2002 | Jethmalani et al. |
| 6,464,725 B2 | 10/2002 | Skottun |
| 6,488,708 B2 | 12/2002 | Sarfarazi |
| 6,493,151 B2 | 12/2002 | Schachar |
| 6,494,910 B1 | 12/2002 | Ganem et al. |
| 6,494,911 B2 | 12/2002 | Cumming |
| 6,503,276 B2 | 1/2003 | Lang et al. |
| 6,506,212 B2 | 1/2003 | Zhou et al. |
| 6,520,691 B2 | 2/2003 | Nomura et al. |
| 6,524,340 B2 | 2/2003 | Israel |
| 6,552,860 B1 | 4/2003 | Alden |
| 6,554,860 B2 | 4/2003 | Hoffmann et al. |
| 6,558,420 B2 | 5/2003 | Green |
| 6,570,718 B2 | 5/2003 | Nomura et al. |
| 6,592,621 B1 | 7/2003 | Domino |
| 6,596,026 B1 | 7/2003 | Gross et al. |
| 6,599,317 B1 | 7/2003 | Weinschenk, III et al. |
| 6,605,093 B1 | 8/2003 | Blake |
| 6,616,692 B1 | 9/2003 | Glick et al. |
| 6,638,305 B2 | 10/2003 | Laguette |
| 6,638,306 B2 | 10/2003 | Cumming |
| 6,645,245 B1 | 11/2003 | Preussner |
| 6,645,246 B1 | 11/2003 | Weinschenk, III et al. |
| 6,730,123 B1 | 5/2004 | Klopotek |
| 6,733,122 B1 | 5/2004 | Feurer et al. |
| 6,739,722 B2 | 5/2004 | Laguette et al. |
| 6,749,634 B2 | 6/2004 | Hanna |
| 6,790,232 B1 | 9/2004 | Lang |
| 6,818,017 B1 | 11/2004 | Shu |
| 6,836,374 B2 | 12/2004 | Esch et al. |
| 6,849,091 B1 | 2/2005 | Cumming |
| 6,851,804 B2 | 2/2005 | Jethmalani et al. |
| 6,855,164 B2 | 2/2005 | Glazier |
| 6,860,601 B2 | 3/2005 | Shadduck |
| 6,930,838 B2 | 8/2005 | Schachar |
| 6,935,743 B2 | 8/2005 | Shadduck |
| 6,960,231 B2 | 11/2005 | Tran |
| 6,966,649 B2 | 11/2005 | Shadduck |
| 6,972,033 B2 | 12/2005 | McNicholas |
| 7,008,449 B2 | 3/2006 | Willis et al. |
| 7,025,783 B2 | 4/2006 | Brady et al. |
| 7,037,338 B2 | 5/2006 | Nagamoto |
| 7,060,094 B2 | 6/2006 | Shahinpoor et al. |
| 7,068,439 B2 | 6/2006 | Esch et al. |

(56) References Cited

U.S. PATENT DOCUMENTS

| | | |
|---|---|---|
| 7,097,660 B2 | 8/2006 | Portney |
| 7,118,596 B2 | 10/2006 | Zadno-Azizi et al. |
| 7,118,597 B2 | 10/2006 | Miller et al. |
| 7,122,053 B2 | 10/2006 | Esch |
| 7,137,994 B2 | 11/2006 | de Juan, Jr. et al. |
| 7,217,288 B2 | 5/2007 | Esch et al. |
| 7,220,279 B2 | 5/2007 | Nun |
| 7,229,476 B2 | 6/2007 | Azar |
| 7,247,168 B2 | 7/2007 | Esch et al. |
| 7,256,943 B1 | 8/2007 | Kobrin et al. |
| 7,261,737 B2 | 8/2007 | Esch et al. |
| 7,278,739 B2 | 10/2007 | Shadduck |
| 7,293,873 B2 | 11/2007 | Dai et al. |
| 7,341,599 B1 | 3/2008 | Peyman |
| 7,350,916 B2 | 4/2008 | Hong et al. |
| 7,369,321 B1 | 5/2008 | Ren et al. |
| 7,381,221 B2 | 6/2008 | Lang et al. |
| 7,384,429 B2 | 6/2008 | Hanna |
| 7,438,723 B2 | 10/2008 | Esch |
| 7,453,646 B2 | 11/2008 | Lo |
| 7,485,144 B2 | 2/2009 | Esch |
| 7,601,169 B2 | 10/2009 | Phillips |
| 7,615,056 B2 | 11/2009 | Ayton et al. |
| 7,637,947 B2 | 12/2009 | Smith et al. |
| 7,675,686 B2 | 3/2010 | Lo et al. |
| 7,763,069 B2 | 7/2010 | Brady et al. |
| 7,776,088 B2 | 8/2010 | Shadduck |
| 7,815,678 B2 | 10/2010 | Ben Nun |
| 7,842,087 B2 | 11/2010 | Ben Nun |
| 7,854,764 B2 | 12/2010 | Ben Nun |
| 7,976,520 B2 | 7/2011 | Nun |
| 7,985,253 B2 | 7/2011 | Cumming |
| 7,988,285 B2 | 8/2011 | Sandstedt et al. |
| 7,998,199 B2 | 8/2011 | Ben Nun |
| 8,018,658 B2 | 9/2011 | Lo |
| 8,034,106 B2 | 10/2011 | Mentak et al. |
| 8,048,156 B2 | 11/2011 | Geraghty et al. |
| 8,158,712 B2 | 4/2012 | Your |
| 8,314,927 B2 | 11/2012 | Choi et al. |
| 8,343,216 B2 | 1/2013 | Brady et al. |
| 8,377,125 B2 | 2/2013 | Kellan |
| 8,414,646 B2 | 4/2013 | De Juan, Jr. et al. |
| 8,663,235 B2 | 3/2014 | Tassignon |
| 8,668,734 B2 | 3/2014 | Hildebrand et al. |
| 8,851,670 B2 | 10/2014 | Dai et al. |
| 8,900,298 B2 | 12/2014 | Anvar et al. |
| 8,956,408 B2 | 2/2015 | Smiley et al. |
| 8,968,396 B2 | 3/2015 | Matthews et al. |
| 8,974,526 B2 | 3/2015 | Bogaert |
| 9,005,282 B2 | 4/2015 | Chang et al. |
| 9,044,317 B2 | 6/2015 | Hildebrand et al. |
| 9,114,005 B2 | 8/2015 | Simonov et al. |
| 9,326,846 B2 | 5/2016 | Devita Gerardi et al. |
| 9,421,089 B2 | 8/2016 | Zadno-Azizi |
| 2001/0001836 A1 | 5/2001 | Cumming |
| 2002/0103535 A1 | 8/2002 | Portney |
| 2002/0103537 A1 | 8/2002 | Willis et al. |
| 2003/0060878 A1 | 3/2003 | Shadduck |
| 2003/0060881 A1 | 3/2003 | Glick et al. |
| 2003/0097177 A1 | 5/2003 | Tran |
| 2003/0109926 A1 | 6/2003 | Portney |
| 2003/0149480 A1 | 8/2003 | Shadduck |
| 2003/0171809 A1 | 9/2003 | Phillips |
| 2003/0187504 A1 | 10/2003 | Weinschenk et al. |
| 2004/0006387 A1 | 1/2004 | Kelman |
| 2004/0034417 A1 | 2/2004 | Heyman |
| 2004/0039446 A1 | 2/2004 | McNicholas |
| 2004/0073304 A1 | 4/2004 | Weinschenk et al. |
| 2004/0082993 A1 | 4/2004 | Woods |
| 2004/0082995 A1 | 4/2004 | Woods |
| 2004/0111153 A1 | 6/2004 | Woods et al. |
| 2004/0148022 A1 | 7/2004 | Eggleston |
| 2004/0162612 A1 | 8/2004 | Portney et al. |
| 2004/0169816 A1 | 9/2004 | Esch |
| 2004/0169820 A1 | 9/2004 | Dai et al. |
| 2004/0181279 A1 | 9/2004 | Nun |
| 2004/0237971 A1 | 12/2004 | Radhakrishnan et al. |
| 2005/0015143 A1 | 1/2005 | Willis et al. |
| 2005/0021138 A1 | 1/2005 | Woods |
| 2005/0060032 A1 | 3/2005 | Magnante et al. |
| 2005/0065534 A1 | 3/2005 | Hohl |
| 2005/0090896 A1 | 4/2005 | Ben Nun |
| 2005/0113914 A1 | 5/2005 | Miller et al. |
| 2005/0125059 A1 | 6/2005 | Pinchuk et al. |
| 2005/0137703 A1 | 6/2005 | Chen |
| 2005/0177229 A1 | 8/2005 | Boxer Wachler |
| 2005/0251253 A1 | 11/2005 | Gross |
| 2006/0047340 A1 | 3/2006 | Brown |
| 2006/0064162 A1 | 3/2006 | Klima |
| 2006/0069431 A1 | 3/2006 | Graney et al. |
| 2006/0069433 A1 | 3/2006 | Nun |
| 2006/0074487 A1 | 4/2006 | Gilg |
| 2006/0100701 A1 | 5/2006 | Esch et al. |
| 2006/0259138 A1 | 11/2006 | Peyman |
| 2007/0010881 A1 | 1/2007 | Soye et al. |
| 2007/0027538 A1 | 2/2007 | Aharoni et al. |
| 2007/0027541 A1 | 2/2007 | Aharoni et al. |
| 2007/0054131 A1 | 3/2007 | Stewart |
| 2007/0088433 A1 | 4/2007 | Esch et al. |
| 2007/0093891 A1 | 4/2007 | Tabernero et al. |
| 2007/0123981 A1 | 5/2007 | Tassignon |
| 2007/0123982 A1 | 5/2007 | Yablonski et al. |
| 2007/0129798 A1 | 6/2007 | Chawdhary |
| 2007/0129799 A1 | 6/2007 | Schedler |
| 2007/0129800 A1 | 6/2007 | Cumming |
| 2007/0129801 A1 | 6/2007 | Cumming |
| 2007/0129803 A1 | 6/2007 | Cumming et al. |
| 2007/0185574 A1 | 8/2007 | Ben Nun |
| 2007/0244561 A1 | 10/2007 | Ben Nun |
| 2008/0004699 A1 | 1/2008 | Ben Nun |
| 2008/0046075 A1 | 2/2008 | Esch et al. |
| 2008/0046076 A1 | 2/2008 | Rombach |
| 2008/0097459 A1 | 4/2008 | Kammerlander et al. |
| 2008/0106698 A1 | 5/2008 | Dai et al. |
| 2008/0119864 A1 | 5/2008 | Deinzer et al. |
| 2008/0125862 A1 | 5/2008 | Blake |
| 2008/0129962 A1 | 6/2008 | Dai et al. |
| 2008/0188930 A1 | 8/2008 | Mentak et al. |
| 2008/0300680 A1 | 12/2008 | Joshua |
| 2009/0171458 A1 | 7/2009 | Kellan et al. |
| 2009/0198247 A1 | 8/2009 | Ben Nun |
| 2009/0234449 A1 | 9/2009 | De Juan, Jr. et al. |
| 2009/0264998 A1 | 10/2009 | Mentak et al. |
| 2010/0121444 A1 | 5/2010 | Ben Nun |
| 2011/0054600 A1 | 3/2011 | Bumbalough |
| 2013/0110235 A1 | 5/2013 | Schwiegerling |
| 2013/0116781 A1 | 5/2013 | Ben Nun |
| 2013/0245754 A1 | 9/2013 | Blum et al. |
| 2014/0228949 A1 | 8/2014 | Argento et al. |
| 2015/0257874 A1 | 9/2015 | Hildebrand et al. |

FOREIGN PATENT DOCUMENTS

| | | |
|---|---|---|
| EP | 637503 A1 | 2/1995 |
| EP | 1 321 112 A1 | 6/2003 |
| EP | 1917932 A1 | 5/2008 |
| EP | 1932492 A1 | 6/2008 |
| FR | 2 794 965 A1 | 12/2000 |
| JP | 2005007029 A | 1/2005 |
| JP | 2005-169131 A | 6/2005 |
| JP | 2005-533611 A | 11/2005 |
| JP | 2009-532176 A | 9/2009 |
| JP | 2011-500270 A | 1/2011 |
| TW | 523408 B | 3/2003 |
| WO | WO-83/00998 A1 | 3/1983 |
| WO | WO-94/28825 A1 | 12/1994 |
| WO | WO-95/20367 A1 | 8/1995 |
| WO | WO-98/05273 A1 | 2/1998 |
| WO | WO-98/10717 A1 | 3/1998 |
| WO | WO-99/62434 A1 | 12/1999 |
| WO | WO-00/30566 A1 | 6/2000 |
| WO | WO-00/61036 A1 | 10/2000 |
| WO | WO-00/66037 A1 | 11/2000 |
| WO | WO-01/08606 A1 | 2/2001 |

(56) References Cited

FOREIGN PATENT DOCUMENTS

| | | |
|---|---|---|
| WO | WO-01/60286 A1 | 8/2001 |
| WO | WO-02/065951 A2 | 8/2002 |
| WO | WO-03/000154 A2 | 1/2003 |
| WO | WO-03/015669 A1 | 2/2003 |
| WO | WO-03/017867 A2 | 3/2003 |
| WO | WO-2004/010905 A2 | 2/2004 |
| WO | WO-2004/037122 A2 | 5/2004 |
| WO | WO-2004/037127 A2 | 5/2004 |
| WO | WO-2004/053568 A1 | 6/2004 |
| WO | WO-2004/107024 A1 | 12/2004 |
| WO | WO-2005057272 A2 | 6/2005 |
| WO | WO-2005/082285 A1 | 9/2005 |
| WO | WO-2005/104994 A2 | 11/2005 |
| WO | WO-2006/040759 A1 | 4/2006 |
| WO | WO-2006/103674 A2 | 10/2006 |
| WO | WO-2007/048615 A1 | 5/2007 |
| WO | WO-2007/113832 A2 | 10/2007 |
| WO | WO-2007/117476 A2 | 10/2007 |
| WO | WO-2008/023379 A2 | 2/2008 |
| WO | WO-2008/031231 A1 | 3/2008 |
| WO | WO-2008/083283 A2 | 7/2008 |
| WO | WO-2008/097915 A1 | 8/2008 |
| WO | WO-2008/107882 A2 | 9/2008 |
| WO | WO-2009/055099 A1 | 4/2009 |
| WO | WO-2009/122409 A1 | 10/2009 |
| WO | WO-2010/010565 A2 | 1/2010 |
| WO | WO-2012/023133 A1 | 2/2012 |

OTHER PUBLICATIONS

U.S. Appl. No. 14/621,305, filed Feb. 12, 2015, US 2015/0150676.
U.S. Appl. No. 15/300,116, filed Sep. 28, 2016, US 2017/0181850.
Chu, Ralph Y. and Buliano, Megan, Accommodating IOLS by Ralph Chu et al, Cataract & Refractive Surgery Today, May 2004. 21 pages.
Notification of Transmittal of the International Preliminary Report on Patentability for PCT/IL2009/000728 filed Jul. 26, 2009 (having a priority date of Jul. 24, 2008). 18 pages.

FOLDABLE ACCOMMODATING INTRAOCULAR LENS

This application is a continuation application of U.S. patent application Ser. No. 14/486,027, filed Sep. 15, 2014, issued as U.S Pat. No. 9,814,568 which is a continuation of U.S. patent application Ser. No. 13/604,172, filed Sep. 5, 2012, issued as U.S. Pat. No. 8,834,565 on Sep. 16, 2014, which is a continuation application of U.S. patent application Ser. No. 11/910,133, filed May 21, 2008 (now abandoned), which was a national stage application for PCT/IL2006/000406, filed Mar. 30, 2006, claiming priority to U.S. Provisional Patent Application Nos. 60/666,180, filed Mar. 30, 2005, U.S. 60/672,081, filed Apr. 18, 2005, and U.S. 60/724,896, filed Oct. 11, 2005, all of which are incorporated herein by reference in their entireties.

FIELD OF THE INVENTION

The invention pertains to accommodating intraocular lens assemblies.

BACKGROUND OF THE INVENTION

Commonly owned PCT International Application No. PCT/IL02/00693 entitled Accommodating Lens Assembly and published on 27 Feb. 2003 under PCT International Publication No. WO 03/015669 illustrates and describes accommodating intraocular lens (hereinafter AIOL) assemblies, the contents of which are incorporated herein by reference. The AIOL assemblies each include a haptics system adapted to be securely fixed in a human eye's annular ciliary sulcus at at least two spaced apart stationary anchor points so that it may act as a reference plane for an AIOL of continuously variable Diopter strength affected by a human eye's capsular diaphragm under control of its sphincter-like ciliary body and acting thereagainst from a posterior direction. The haptics systems include a rigid planar haptics plate with a telescoping haptics member for sliding extension. The haptics plate and the haptics member are preferably self-anchoring as illustrated and described in commonly owned PCT International Application No. PCT/IL02/00128 entitled Intraocular Lens and published on 29 Aug. 2002 under PCT International Publication No. WO 02/065951, the contents of which are incorporated herein by reference.

Commonly owned PCT International Application No. PCT/IL2005/000456 entitled Accommodating Intraocular Lens Assemblies and Accommodation Measurement Implant and published on 10 Nov. 2005 under PCT International Publication No. WO 2005/104994 illustrates and describes AIOL assemblies enabling post implantation in situ manual selective displacement of an AIOL along a human eye's visual axis relative to at least two spaced apart stationary anchor points to a desired position to ensure that an AIOL assumes a non-compressed state in a human eye's constricted ciliary body state. Such in situ manual selective displacement can be effected post implantation to correct for capsular contraction which is a natural reaction which typically develops over a few months following extraction of the contents of a human eye's natural crystalline lens, and also a subject's changing eyesight overtime with minimal clinical intervention. Such in situ manual selective displacement can be achieved as follows: First, a discrete haptics system for retaining a discrete AIOL which is manually displaceable relative thereto. And second, a haptics system with at least two haptics having radiation sensitive regions capable of undergoing plastic deformation for in situ manual displacement of an integrally formed AIOL.

Commonly owned PCT International Application No. PCT/IL2005/001069 entitled Accommodating Intraocular Lens (AIOL), and AIOL Assemblies Including Same illustrates and describes an AIOL including a biasing mechanism for elastically deforming an elastically deformable shape memory disk-like optical element for affording the AIOL a natural positive Diopter strength for near vision. The AIOL is intended to be implanted in a human eye such that relaxation of its ciliary body causes its capsular diaphragm to apply an external force for overcoming the biasing mechanism to reduce the AIOL's natural positive Diopter strength for distance vision.

Other AIOLs are illustrated and described in U.S. Pat. No. 4,254,509 to Tennant, U.S. Pat. No. 4,409,691 to Levy, U.S. Pat. No. 4,888,012 to Horn et al., U.S. Pat. No. 4,892,543 to Turley, U.S. Pat. No. 4,932,966 to Christie et al., U.S. Pat. No. 5,476,514 to Cumming, U.S. Pat. No. 5,489,302 to Skottun, U.S. Pat. No. 5,496,366 to Cumming, U.S. Pat. No. 5,522,891 to Klaas, U.S. Pat. No. 5,674,282 to Cumming, U.S. Pat. No. 6,117,171 to Skottun, U.S. Pat. No. 6,197,059 to Cumming, U.S. Pat. No. 6,299,641 to Woods, U.S. Pat. No. 6,342,073 to Cumming et al., U.S. Pat. No. 6,387,126 to Cumming, U.S. Pat. No. 6,406,494 to Laguette et al., U.S. Pat. No. 6,423,094 to Sarfarazi, U.S. Pat. No. 6,443,985 to Woods, U.S. Pat. No. 6,464,725 to Skotton, U.S. Pat. No. 6,494,911 to Cumming, U.S. Pat. No. 6,503,276 to Lang et al., U.S. Pat. No. 6,638,306 to Cumming, U.S. Pat. No. 6,645,245 to Preussner, US Patent Application Publication No. US 2004/0169816 to Esch, and EP 1 321 112.

SUMMARY OF THE INVENTION

One aspect of the present invention is directed towards accommodating intraocular (AIOL) assemblies each including at least one shape memory optical element resiliently elastically deformable between a non-compressed shape with a first Diopter strength and a compressed shape with a second Diopter strength different than its first Diopter strength such that an AIOL has a continuously variable Diopter strength between a minimum Diopter strength for distance vision purposes and a maximum Diopter strength for near vision purposes. The AIOL assemblies are intended for in situ manual selective displacement of an AIOL along a human eye's visual axis relative to stationary anchor points after implantation for enabling accurate AIOL deployment to take full advantage of the reciprocal movement of a human eye's capsular diaphragm between its constricted ciliary body position and its relaxed ciliary body position. Axial displacement may be over a continuous range in a similar manner to aforesaid WO 2005/104994 or alternatively at discrete axial stopping positions typically from about 100 µm to about 300 µm apart. Stepwise axial displacement is preferably enabled by a so-called "push and twist" bayonet arrangement similar to a conventional light bulb fitting having a single stopping position. The AIOL assemblies each include a haptics system also suitable for self-anchoring implantation of a fixed Diopter strength IOL in a human eye as opposed to an AIOL having a variable Diopter strength.

Another aspect of the present invention is directed towards AIOLs which lend themselves to be at least partially folded under reasonable forces as can be applied using conventional ophthalmic surgical tools, for example, tweezers, for facilitating insertion into a human eye through a relatively small incision. The AIOLs can be provided as discrete components for use with discrete haptics systems for enabling aforesaid in situ axial displacement. The discrete ATMs are provided with typically two or more manipulation apertures accessible from an anterior side for receiving the tip of a handheld manipulation tool for enabling in situ manipulation. The manipulation apertures may be in the form of peripheral disposed manipulation rings, blind manipulation notches, and the like. Alternatively, the AIOLs can be integrally formed with a haptics system including at least two elongated haptics having radiation sensitive regions capable of undergoing plastic deformation for enabling aforesaid in situ axial displacement.

BRIEF DESCRIPTION OF THE DRAWINGS

In order to understand the invention and to see how it can be carried out in practice, preferred embodiments will now be described, by way of non-limiting examples only, with reference to the accompanying drawings in which similar parts are likewise numbered, and in which.

DETAILED DESCRIPTION OF PREFERRED EMBODIMENTS OF THE PRESENT INVENTION

Figure 1:
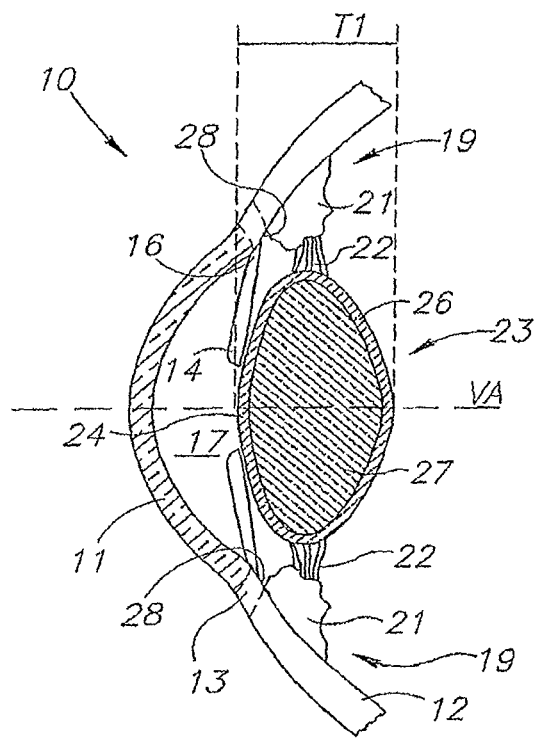
FIG. 1 is a cross section view of an anterior part of a human eye in its natural near vision condition in an axial plane of the human body.
Figure 2:
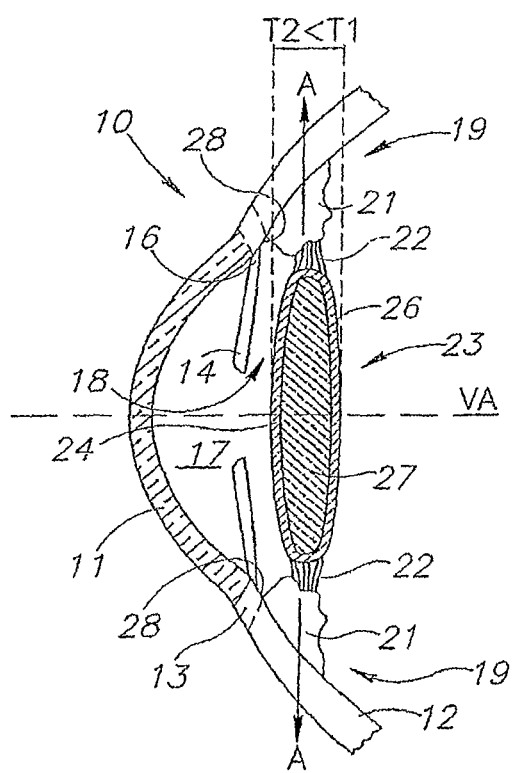
FIG. 2 is a cross section view of an anterior part of a human eye in its natural distance vision condition in an axial plane of the human body.

FIGS. 1 and 2 are cross section views of an anterior part of a human eye 10 having a visual axis VA in its natural near and distance vision conditions, respectively, in an axial plane of the human body. The human eye 10 has a cornea 11 peripherally connected to a spherical exterior body made of tough connective tissue known as the sclera 12 at an annular sclero-corneal juncture 13. An iris 14 inwardly extends into the human eye 10 from its root 16 at the sclero-corneal juncture 13 to divide the human eye's anterior part into an anterior chamber 17 and a posterior chamber 18. A sphincter-like peripheral structure known as the ciliary body 19 includes ciliary processes housing ciliary muscles 21 fired by parasympathetic nerves. The ciliary muscles 21 are connected to zonular fibers 22 which in turn are peripherally connected to the equatorial edge of a membrane known as the capsular bag 23 with an anterior capsule 24 and a posterior capsule 26 enrobing a natural crystalline lens 27. The iris's root 16 and the ciliary body 19 delimit a portion of the interior surface of the sclera 12 at the sclero-corneal juncture 13 known as the ciliary sulcus 28. Remnants of the anterior capsule 24 which may remain after extraction of the natural crystalline lens 27 and the intact posterior capsule 26 are referred to hereinafter as the capsular diaphragm 29. Contraction of the ciliary body 19 allows the lens 27 to thicken to its natural thickness T1 along the visual axis VA for greater positive optical power for near vision (see FIG. 1). Relaxation of the ciliary body 19 tensions the zonular fibers 22 which draws the capsular bag 23 radially outward as shown by arrows A for compressing the lens 27 to shorten its thickness along the visual axis VA to T2<T1 for lower positive optical power for distance vision (see FIG. 2).

Figure 3:
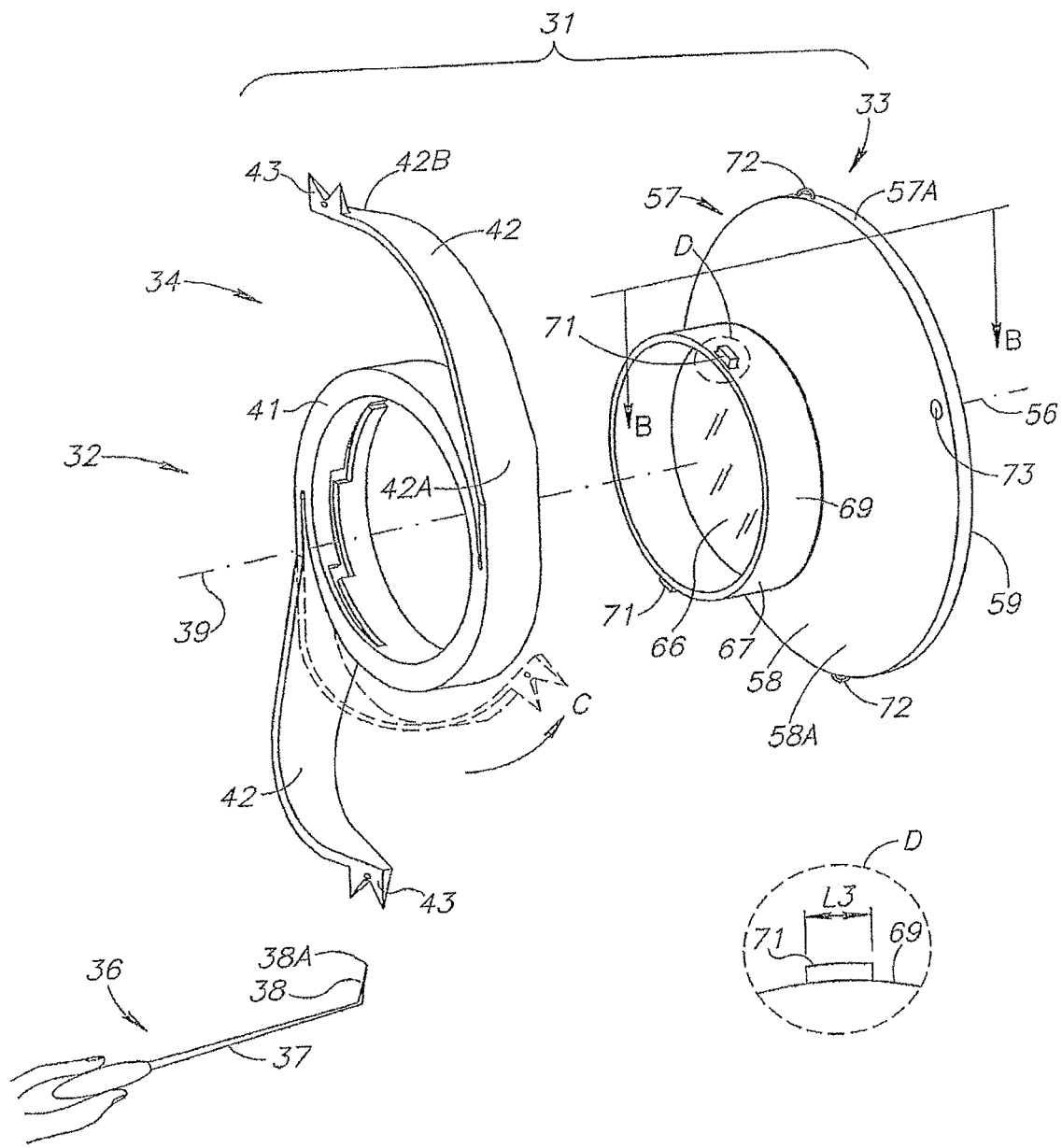
FIG. 3 is a pictorial view of a disassembled "push and twist" AIOL assembly including a discrete haptics system and a discrete AIOL with a flattened spherical shaped housing a shape memory optical element.

FIG. 3 shows a "push and twist" AIOL assembly 31 for self-anchoring in a human eye's ciliary sulcus 28 for preferably enabling spectacle free vision over the nominal range of human vision. The AIOL assembly 31 includes a discrete haptics system 32 for selectively retaining a discrete AIOL 33, and a "push and twist" bayonet arrangement 34 for effecting stepwise axial displacement of the AIOL 33 relative to the haptics system 32 and therefore along a human eye's visual axis. A handheld manipulation tool 36 with an elongated shaft 37 and an inclined end piece 38 with a tip 38A is employed for assembling the AIOL assembly 31 in situ and for manipulating the AIOL 33 for stepwise axial displacement relative to the haptics system 32.

The haptics system 32 is made from suitable rigid biocompatible transparent polymer material such as PMMA, and the like. The haptics system 32 has a longitudinal axis 39 intended to be co-directional with a human eye's visual axis. The haptics system 32 includes a tubular main body 41 with a diameter D1 in the region of 4 mm-5 mm corresponding to a human eye's pupil, and an axial length L1 of 1 mm±0.5 min along the longitudinal axis 39 (see FIG. 10). The haptics system 32 has a pair of diametrically opposite elongated C-shaped haptics 42 extending from its main body 41 in opposite directions in a plane perpendicular to its longitudinal axis 39. The haptics 42 have a thin profile in the plane perpendicular to the longitudinal axis 39 such that they are sufficiently flexible under reasonable forces as can be applied using conventional ophthalmic surgical tools for encircling around the main body 41 shown by arrow C for facilitating insertion of the haptics system 32 into a human eye through a relatively small incision. FIG. 3 shows a haptics 42 in dashed lines for showing its encircling around the main body 41. The haptics 42 have a wide profile along the longitudinal axis 39 such that they are rigid against a compression force therealong. The haptics' wide profile preferably tapers from its proximal end 42A adjacent the main body 41 to its distal end 42B remote therefrom and terminating at a bifurcated attachment plate 43.

Figure 4:
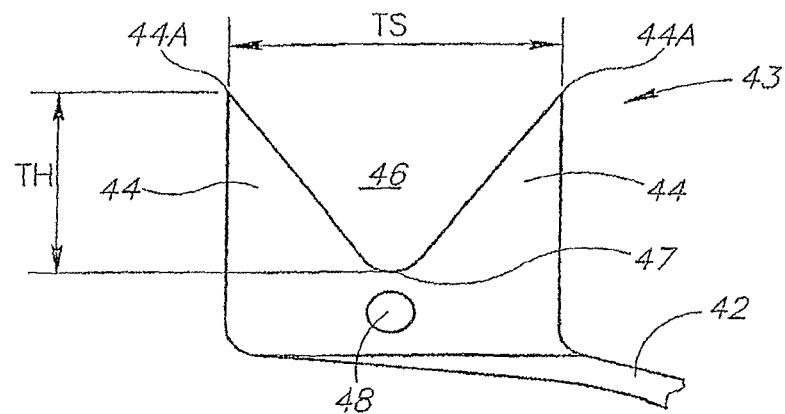
FIG. 4 is a close-up front view of a bifurcated attachment plate of FIG. 3's haptics system.

FIG. 4 shows an attachment plate 43 has a near square shape in a front view in the plane perpendicular to the longitudinal axis 39 and is formed with a pair of spaced apart pointed puncturing members 44 of sufficient strength for forced penetration into the tough connective tissue of a human eye's sclera 12. The attachment plate 43 has an isosceles shaped cutout 46 pointing towards its haptics 42 to leave a central narrow juncture 47 for determining the maximal penetration of the attachment plate 43 into a human eye's sclera 12 on its abutment thereagainst. The puncturing members 44 have tips 44A with a minimum tip separation TS of at least 1 mm and preferably between about 2 mm and 3 mm in the plane perpendicular to the longitudinal axis 39. The puncturing members 44 have a minimum tip height TH of at least 0.5 mm as measured between the tips 44A and the juncture 47 such that they can penetrate slightly more than half of a sclera's thickness of about 1 mm. The tip height TH is preferably between about 0.8 mm and 1.3 mm. The attachment plates 43 are formed with a manipulation aperture 48 in the central portion between the cutout 46 and the haptics 42 for selectively receiving the handheld manipulation tool's tip 38A for in situ manipulation purposes. The manipulation aperture 48 is preferably constituted by an about 0.4 mm diameter throughgoing bore.

Figure 5:
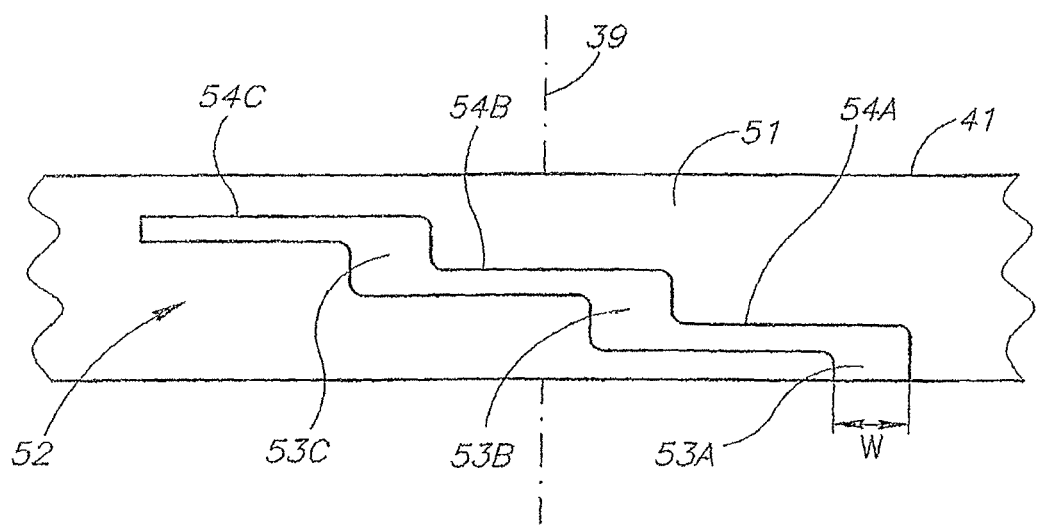
FIG. 5 is a pictorial view of a stepped track of FIG. 3's haptics system.

The main body 41 has an internal surface 51 formed with two or more equidistant stepped tracks 52 only one of which is visible in FIG. 3. FIG. 5 shows a stepped track 52 has three axial directed channels 53A, 53B and 53C enabling axial displacement of the AIOL 33 relative to the haptics system 32 and three peripheral grooves 54A, 54B and 54C enabling rotational displacement of the AIOL 33 relative to the haptics system 32 and precluding inadvertent slipping of the AIOL 33 in an axial direction relative to a human eye's visual axis. The axial directed channels have peripheral widths W. The peripheral grooves 54A correspond to a most posterior stopping position, the peripheral grooves 54B correspond to an intermediate position, and the peripheral grooves 54C correspond to a most anterior position of an AIOL along a human eye's visual axis, respectively.

Figure 8:
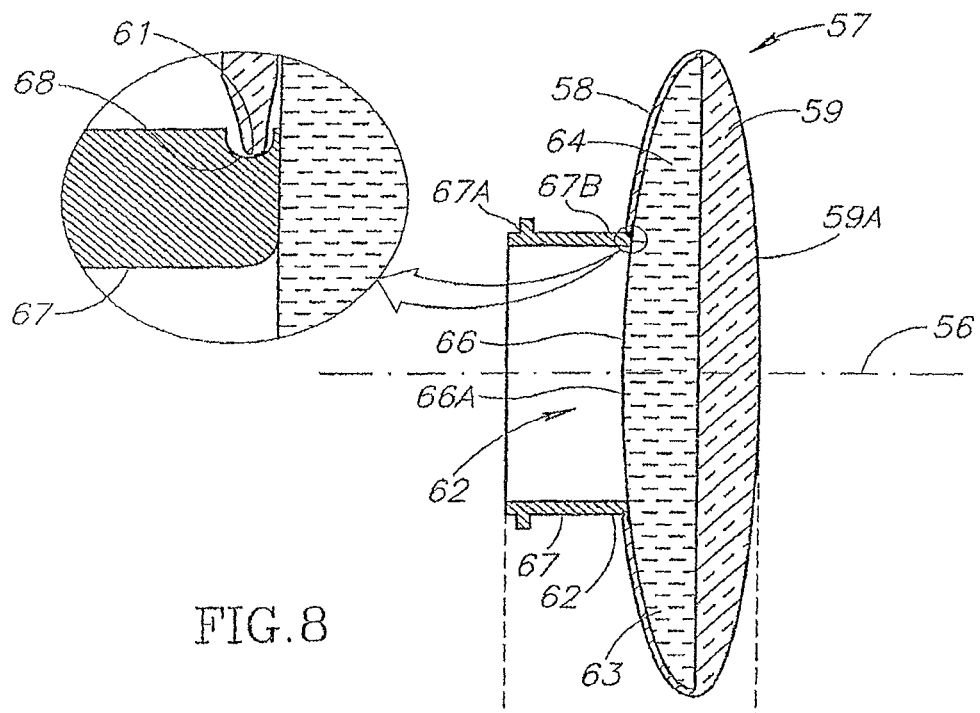
FIG. 8 is a longitudinal cross section view of the FIG. 3's AIOL in its non-compressed state along line B-B in FIG. 3.
Figure 9:
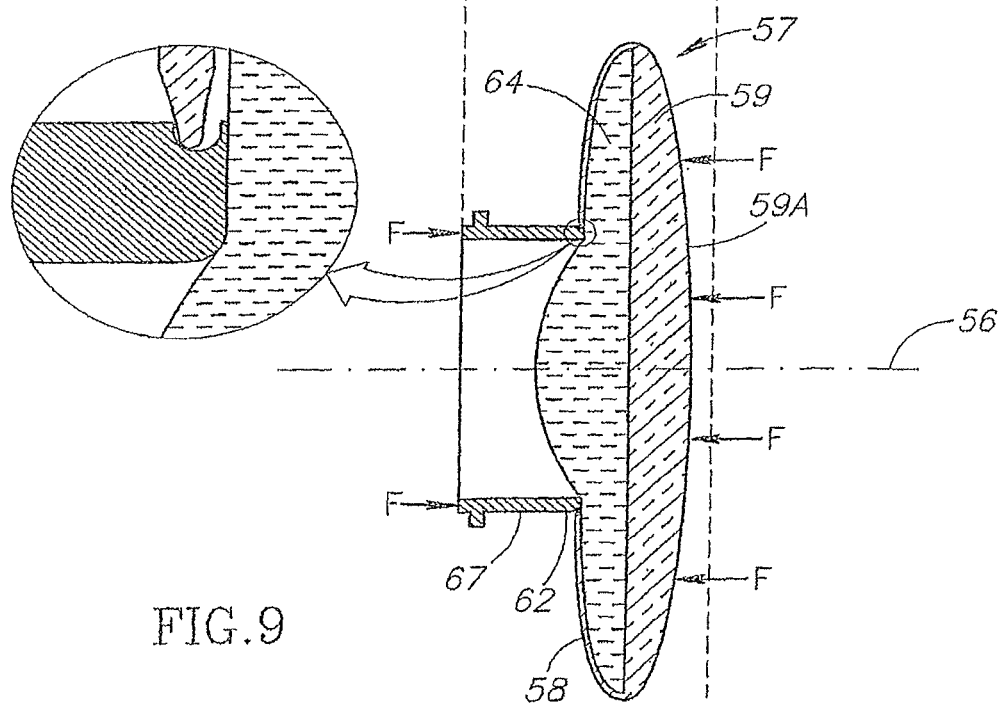
FIG. 9 is a longitudinal cross section of FIG. 3's AIOL in its compressed state along line B-B in FIG. 3.

FIGS. 3, 8 and 9 show the AIOL 33 has a longitudinal axis 56 intended to be co-directional with a human eye's visual axis, and a hollow flattened spherical shaped housing 57, an annular anterior member 58 with a leading surface 58A, and a posterior member 59 having a trailing surface 59A. The leading surface 58A has an internal rim 61 defining an anterior facing aperture 62 having a diameter slightly smaller than that of the main body 41. The housing 57 defines a cavity 63 housing a shape memory optical element 64 with a leading surface 66 with a central portion 66A exposed through the aperture 62. The posterior member 59 can be formed without any optical power or preferably as a plano-convex optical member with positive Diopter strength as shown. The housing 57 has a diameter D2 of at least 6 mm for an adult sized AIOL 33, and preferably of about 7 mm 1 mm so as to bear against a major portion of a human eye's capsular diaphragm 29 (see FIG. 10).

Figure 10:
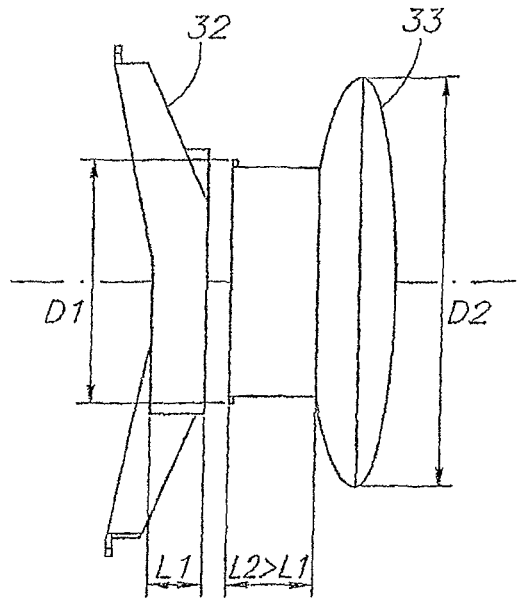
FIG. 10 is a side view of FIG. 3's AIOL assembly prior to assembly.
Figure 11:
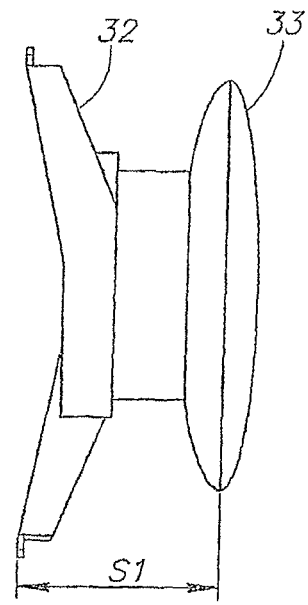
FIG. 11 is a side view of FIG. 3's AIOL assembly at its most posterior axial stopping position.
Figure 12:
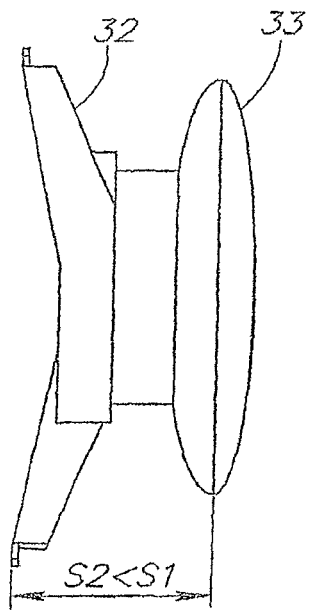
FIG. 12 is a side view of FIG. 3's AIOL assembly at an intermediate axial stopping position.
Figure 13:
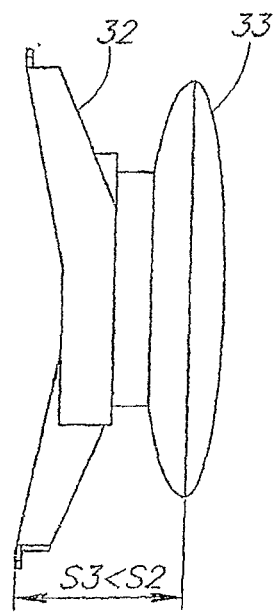
FIG. 13 is a side view of FIG. 3's AIOL assembly at its most anterior axial stopping position.

The AIOL 33 includes a rigid tubular casing 67 having an axial length L2 and a leading end 67A for facing in an anterior direction in a human eye, and a trailing end 67B for facing in a posterior direction in a human eye (see FIG. 10). The trailing end 67B is formed with a groove 68 for receiving the internal rim 61 whereupon the casing 67 can reciprocate relative thereto for selectively compressing the optical element 64. The casing 67 has a peripheral cylindrical surface 69 with lugs 71 for traveling along the stepped tracks 52. The lugs 71 have peripheral lengths L3 where W=L3+Δ. The housing 57 is formed with manipulation rings 72 on its peripheral rim 57A and/or blind manipulation notches 73 on its leading surface 58A for selectively receiving the handheld manipulation tool's tip 38A for enabling in situ manipulation of the AIOL 33 from an anterior direction on implantation of the AIOL 33 in a human eye.

Figure 6:
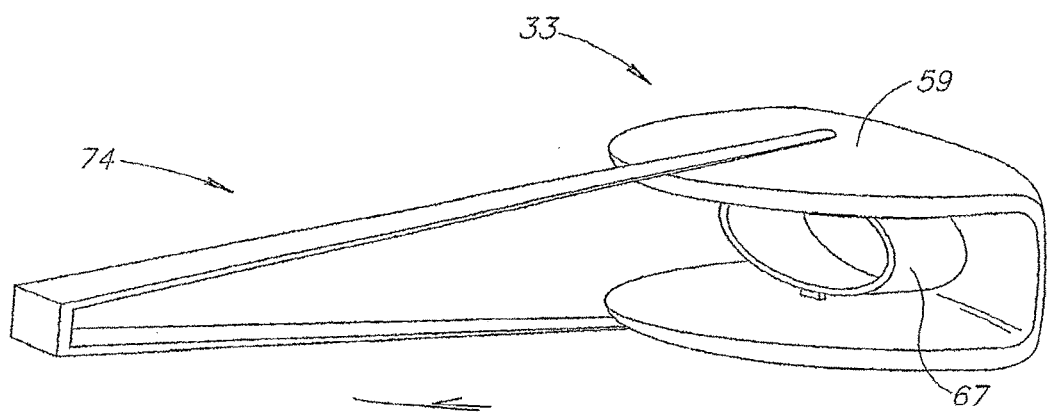
FIG. 6 is a pictorial view of a FIG. 3's AWL being folded by tweezers for insertion into a human eye through a small incision.

The housing 57, the optical element 64 and the casing 67 are preferably formed from suitable biocompatible transparent polymer material of different consistencies which can be elastically deformed under reasonable forces as can be applied using conventional ophthalmic surgical tools, for example, tweezers 74, and the like, for facilitating insertion of the AIOL 33 into a human eye through a relatively small incision (see FIG. 6). The casing 67 is typically formed from a relatively rigid polymer material, for example, PMMA, whilst the housing 57 is formed from less rigid silicone or acrylic based polymer material, and the optical element 64 is formed from still softer silicone gel, or softer acrylic based polymer material. For example, the housing 57 can be formed from MED6400 polymer material and the optical element 64 can be formed from MED3-6300 polymer material both polymer materials being commercially available from NuSil Silicon Technology, Inc., California, USA (www.nusil.com).

Figure 7:
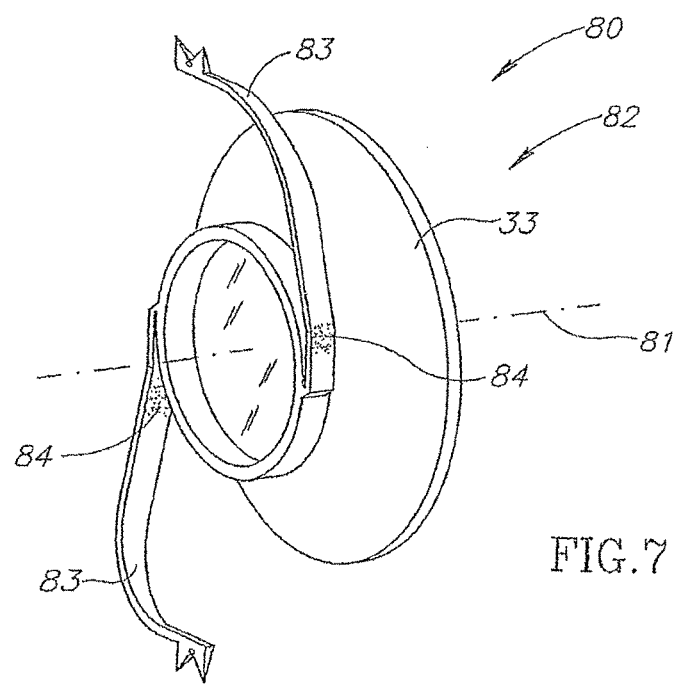
FIG. 7 is a pictorial view of a unitary AIOL assembly including a haptics system integrally formed with FIG. 3's AIOL.

FIG. 7 shows a unitary AIOL assembly 80 having a longitudinal axis 81 intended to be co-directional with a human eye's visual axis, and a haptics system 82 integrally formed with the AIOL 33 which thereby effectively acts as the haptics system's main body. The haptics system 82 includes a pair of diametrically opposite elongated C-shaped haptics 83 extending from its AIOL 33 in opposite directions in a plane perpendicular to the longitudinal axis 81 in a similar manner to the haptics system 32. In this case, the haptics 83 have regions 84 impregnated with radiation sensitive bio-compatible materials such as IR sensitive indocyanine green (ICG), and the like, such that they are capable of being plastically deformed on heating to a so-called glass transmission temperature to enable post implantation in situ axial displacement as illustrated and described in aforesaid WO2005/104994.

FIG. 8 shows the non-compressed shape of the optical element 64 has a continuous slightly curvilinear leading surface 66 including its exposed central portion 66A in the AIOL's non-compressed state. FIG. 9 shows the compressed shape of the optical element 64 bulging anteriorly into the casing 67 on applying a compression force F along its longitudinal axis 39 for compressing the AIOL 33 into its compressed state. The bulging shape is dependent on the compression force and bulges more in its compressed shape than its non-compressed shape whereby the AIOL 33 has a continuously variable Diopter strength from a minimum Diopter strength suitable for distance vision and a maximum Diopter strength suitable for near vision. The optical element 64 typically has a refractive index similar to that of the natural crystalline lens 27 or greater whereupon its non-compressed state is suitable for distance vision and its compressed state is suitable for near vision. In the case that the optical element 64 has a refractive index less than the human eye's aqueous humor, the optical element 64 acts as a concave lens such that its non-compressed state is suitable for near vision and its compressed state is suitable for distance vision.

FIGS. 10-13 show the use of the "push and twist" bayonet arrangement 34 for in situ adjustment of the AIOL 33 along a human eye's visual axis. The AIOL 33 is deployed posterior to the haptics system 32 and is rotated to align its lugs 71 with the channels 53A. The AIOL 33 is displaced in an anterior direction to insert its lugs 71 into the channels 53A and is rotated in a clockwise direction on facing the AIOL 33 from a posterior direction to midway along the grooves 54A for assuming its most posterior position (see FIG. 11). Positioning the AIOL 33 at its intermediate stopping position along a human eye's visual axis denoted by S2<S1 involves a further clockwise rotation of the AIOL 33 relative to the haptics system 32 to reach the channels 53B, displacing the AIOL 33 in an anterior direction along the channels 53B to reach the grooves 54B, and a clockwise rotation of the AIOL 33 relative to the haptics system 32 (see FIG. 12). Positioning the AIOL 33 at its most anterior position along a human eye's visual axis denoted by S3<S2 involves a further clockwise rotation of the AIOL 33 relative to the haptics system 32 to reach the channels 53C, displacing the AIOL 33 in an anterior direction along the channels 53C to reach the grooves 54C, and a further clockwise rotation of the AIOL 33 relative to the haptics system 32 (see FIG. 13).

Figure 14:
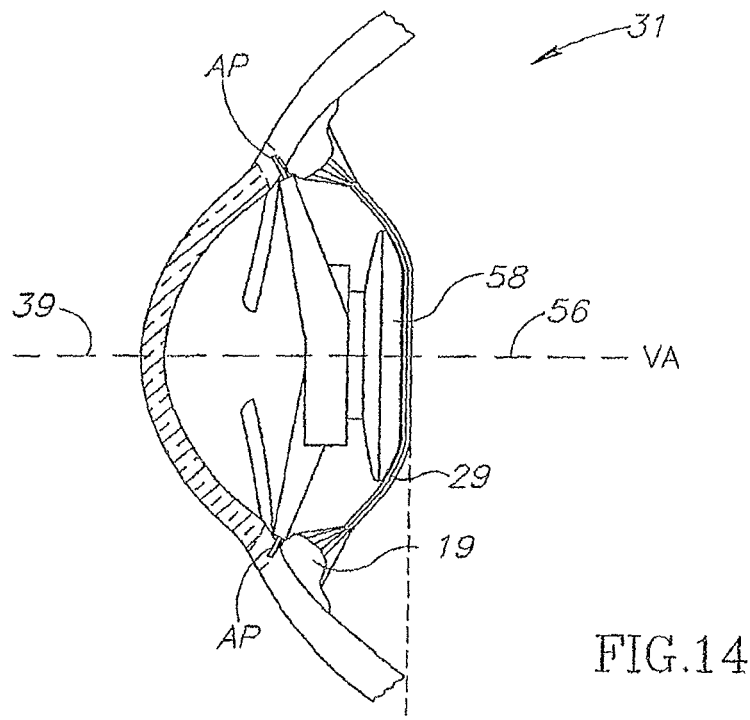
FIG. 14 is a cross section view of an anterior view of a human eye in an axial plane of the human body implanted with FIG. 3's AIOL assembly in an initial position along the human eye's visual axis.
Figure 15:
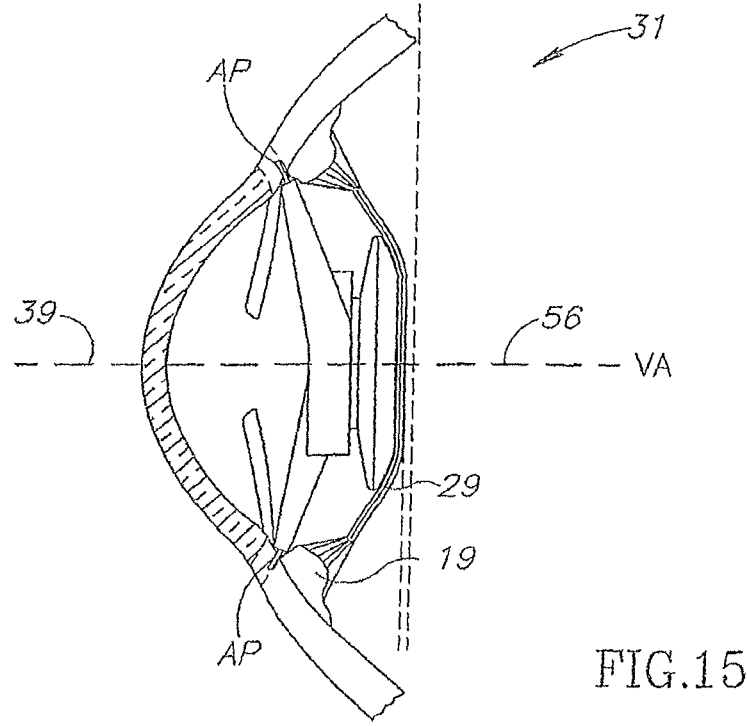
FIG. 15 is a cross section view of an anterior view of a human eye in an axial plane of the human body implanted with FIG. 3's AIOL assembly at a subsequent position along the human eye's visual axis to compensate for capsular contraction.

Implantation of the AIOL assembly 31 in a human eye 10 after removal of its natural crystalline lens 27 to leave its double layered capsular diaphragm 29 including remnants of its anterior capsule 24 overlying its still intact posterior capsule 26 is now described with reference to FIGS. 14 and 15. The AIOL assembly 31 is set up such that the AIOL's longitudinal axis 56 coincides with the haptics system's longitudinal axis 39. The AIOL assembly 31 is typically implanted into a human eye 10 after administration of topical drops of a cycloplegic drug for relaxing its iris muscles, thereby dilating its pupil for facilitating access to its posterior chamber 18 immediately behind its iris 14. Such administration also induces the human eye 10 into its relaxed ciliary body state thereby tensioning its capsular diaphragm 29 which has some slack by virtue of the removal of its natural crystalline lens 27 leaving its capsular diaphragm 29 for accommodation purposes. FIG. 14 shows that the haptics system's puncturing members 44 are forcibly inserted into the sclera 12 at stationary anchor points AP for retaining the AIOL assembly 31 in the annular ciliary sulcus 28. FIG. 14 also shows that the AIOL assembly 31 is deployed such that its longitudinal axes 41 and 56 are co-directional and preferably co-axial with the human eye's visual axis VA and the trailing surface 59A is urged in a posterior direction against the capsular diaphragm 29 tensioning same to become sufficiently taut to urge the AIOL 33 to its compressed state as shown in FIG. 9. The AIOL 33 is so deployed that constriction of the ciliary body 19 is intended to enable the AIOL 33 to assume its non-compressed state as shown in FIG. 8 thereby affording accommodation over the full range of the reciprocal movement of the human eye's capsular diaphragm 29. However, in the case of capsular contraction, the AIOL 33 is unable to assume its fully non-compressed state in the human eye's constricted ciliary body state such that it remains at least partially compressed depending on the degree of the capsular contraction thereby diminishing its accommodation ability. The accommodation ability of the AIOL 33 is restored by moving the AIOL 33 in an anterior direction to either its intermediate stopping position or its most anterior stopping position (see FIG. 15).

Figure 16:
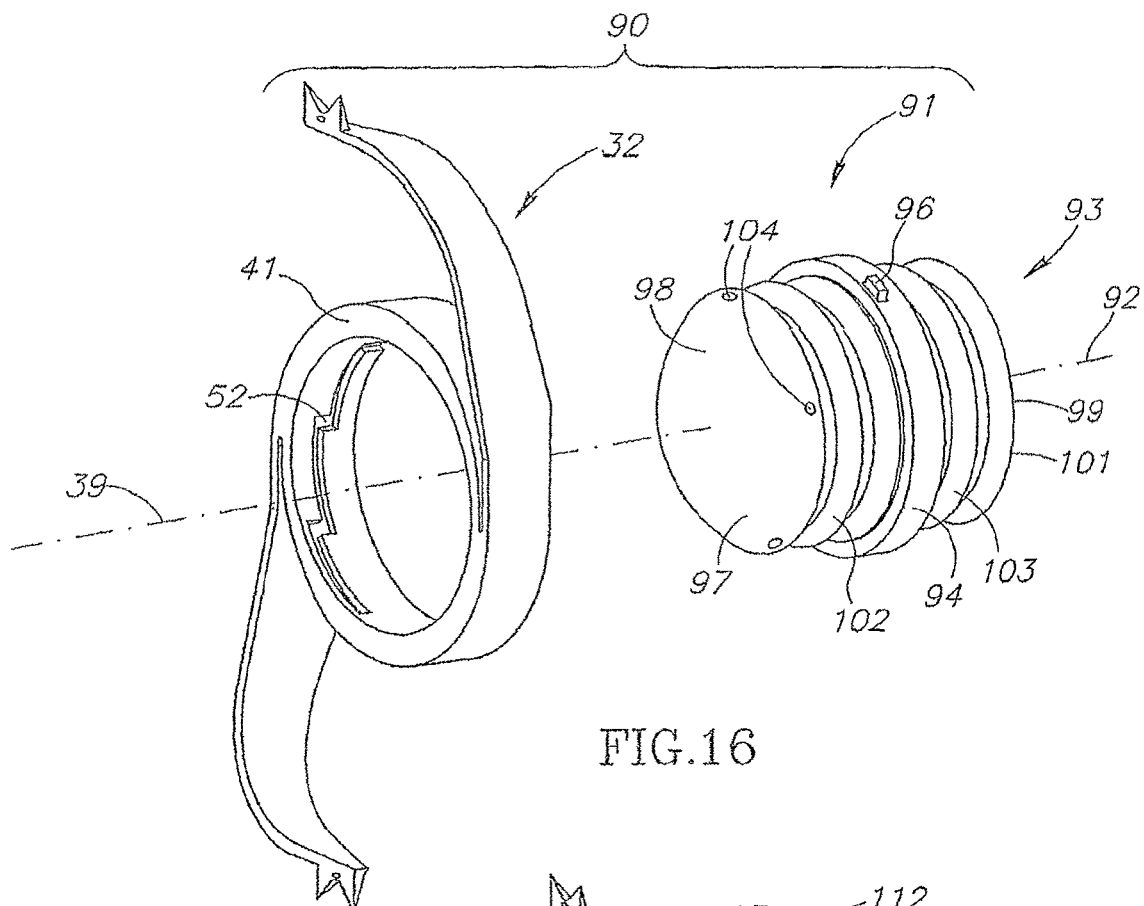
FIG. 16 is a pictorial view of a disassembled "push and twist" AIOL assembly including a discrete haptics system and a discrete dual bellows-like AIOL.

FIG. 16 show an AIOL assembly 90 including a discrete haptics system 32 and a discrete dual bellows-like AIOL 91. The AIOL 91 has a longitudinal axis 92 intended to be co-directional with a human eye's visual axis, and a housing 93 having a ring 94 with lugs 96 for traveling along the stepped tracks 52, an anterior member 97 with a leading surface 98, and a posterior member 99 with a trailing surface 101. The housing 93 includes a leading shape memory resiliently elastically deformable bellows-like optical element 102 between the ring 94 and the anterior member 97, and a trailing shape memory resiliently elastically deformable bellows-like optical element 103 between the ring 94 and the posterior member 99. The anterior member 97 is formed with blind manipulation notches 104 for selectively receiving the handheld manipulation tool's tip 38A for enabling in situ manipulation of the AIOL 33.

The ring 94, the anterior member 97, the posterior member 99, and the optical elements 102 and 103 are preferably formed from suitable polymer based biocompatible transparent material of different consistencies. The ring 94 is typically formed from a relatively rigid polymer material, for example, PMMA, whilst the anterior member 97 and the posterior member 99 are formed from less rigid silicone or acrylic based polymer material, and the optical elements 102 and 103 are formed from still softer silicone gel or softer acrylic based polymer material. For example, the anterior member 97 and the posterior member 99 can be formed from aforesaid MED6400 polymer material and the optical elements 102 and 103 can be formed from aforesaid MED3-6300 polymer material. Alternatively, the ring 94 can be formed with a membrane for dividing the AIOL 91 into two compartments which can be injected with a suitable silicone or water based gel. The anterior member 97 and the posterior member 99 can be formed as flat optical members without any optical power or preferably as plano-convex optical members as shown.

Figure 17:
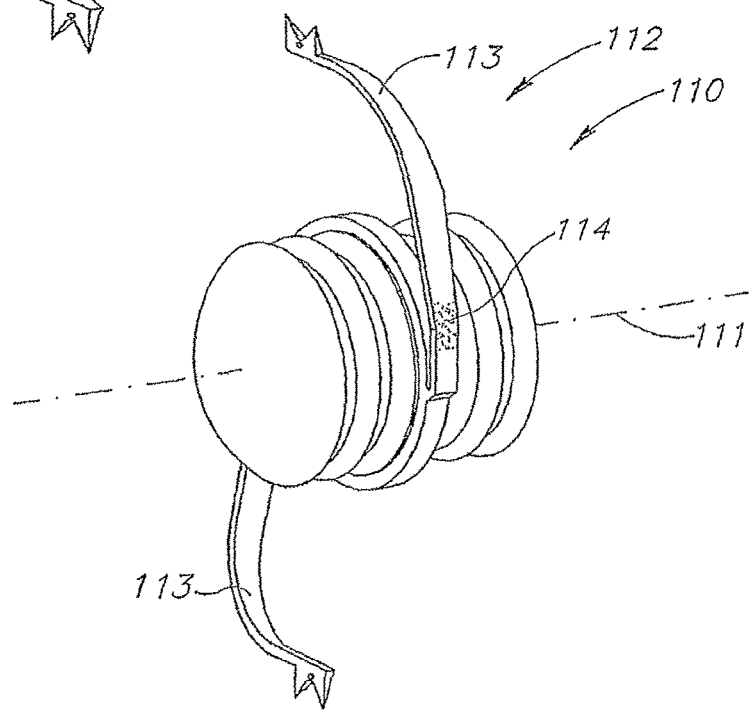
FIG. 17 is a pictorial view of a unitary AIOL assembly including a haptics system integrally formed with FIG. 16's dual bellows-like AIOL.

FIG. 17 shows a unitary AIOL assembly 110 having a longitudinal axis 111 intended for to co-directional with a human eye's visual axis, and a haptics system 112 integrally formed with the AIOL 91 which thereby effectively acts as the haptics system's main body. The haptics system 112 includes a pair of diametrically opposite C-shaped elongated haptics 113 extending from its AIOL 91 in opposite directions in a plane perpendicular to the longitudinal axis 111 in a similar manner to the haptics system 32. In this case, the haptics 113 have regions 114 impregnated with radiation sensitive bio-compatible materials such as IR sensitive indocyanine green (ICG), and the like, such that they are capable of being plastically deformed on heating to a so-called glass transmission temperature to enable post implantation in situ axial displacement as illustrated and described in aforesaid WO2005/104994.

Figure 18:
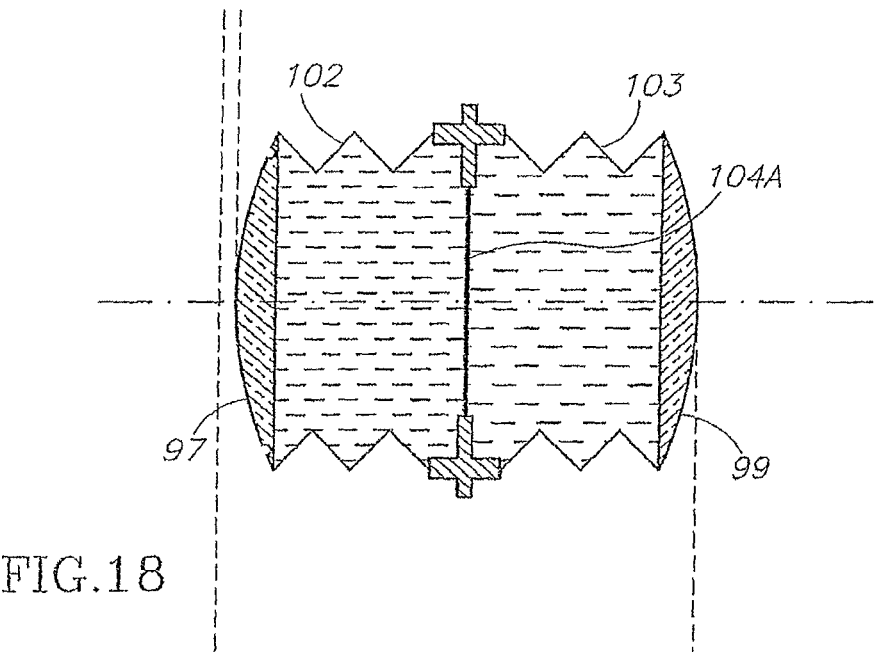
FIG. 18 is a longitudinal cross section view of FIG. 16's dual bellows-like AIOL in its non-compressed state.
Figure 19:
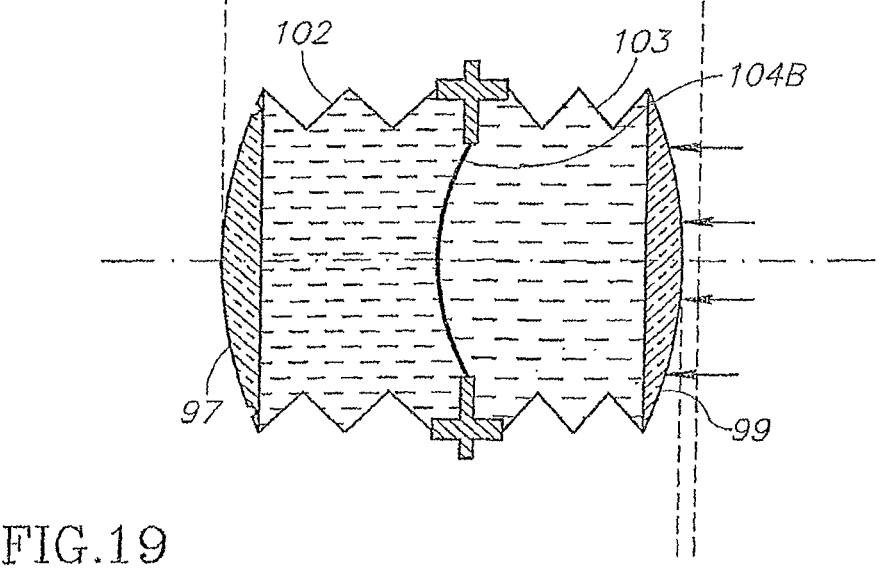
FIG. 19 is a longitudinal cross section of FIG. 16's dual bellows-like AIOL in its compressed state.

FIG. 18 show the non-compressed shapes of the optical elements 102 and 103 having a flat surface 104A in a non-compressed state of AIOL 91. FIG. 19 shows the optical element 103 bulging into the optical element 102 to create a curved surface 104B on applying a compression force F against the trailing surface 101 in the direction of the anterior member 97 on retaining the ring 94 in a fixed position which in turn causes the optical element 102 to expand in an anterior direction for distancing the anterior member 97 away from the ring 94. The optical element 103 bulges more into the optical element 102 with a greater compression force whereby the AIOL 91 has a continuously variable Diopter strength from a minimum Diopter strength suitable for distance vision and a maximum Diopter strength suitable for near vision.

Figure 20:
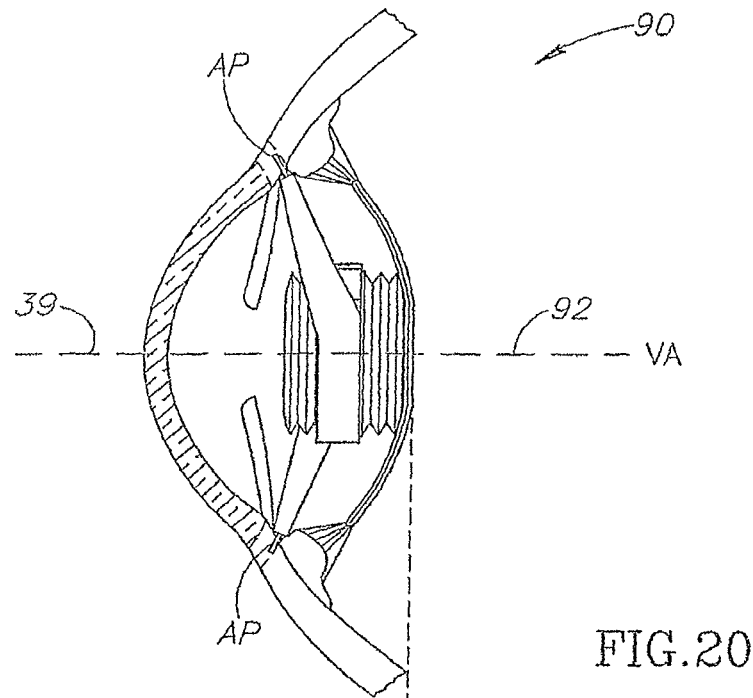
FIG. 20 is a cross section view of an anterior view of a human eye in its contracted ciliary body state in an axial plane of the human body implanted with FIG. 16's AIOL assembly.
Figure 21:
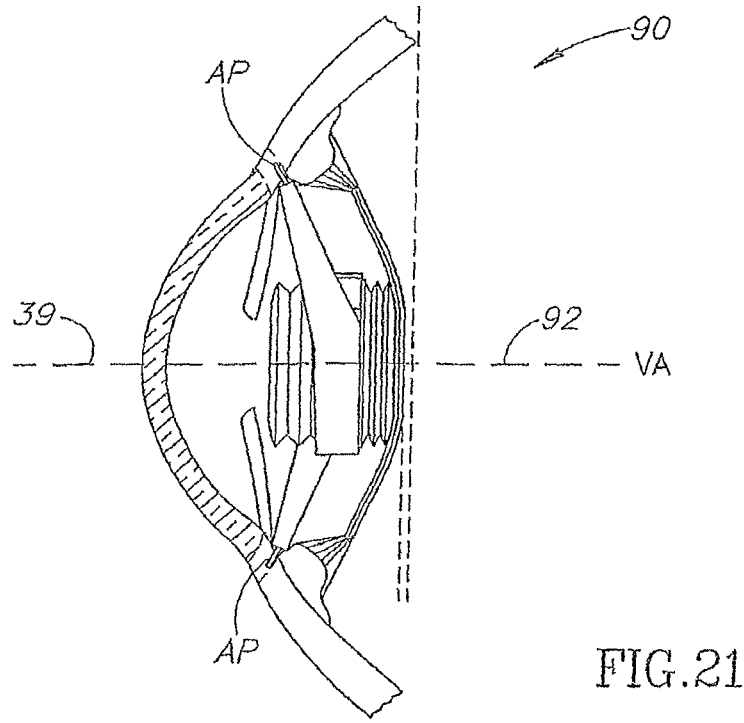
FIG. 21 is a cross section view of an anterior view of a human eye in its relaxed ciliary body state in an axial plane of the human body implanted with FIG. 16's AIOL assembly.

The optical element 102 preferably has a refractive index n2 which is greater than the optical element's refractive index n1 whereby the curved surface 104B acts as a concave lens with a negative optical power such that the AIOL 91 is suitable for near vision in its non-compressed state (see FIGS. 18 and 20) and distance vision in its compressed state (see FIGS. 19 and 21). The AIOL 91 can be engineered to produce very high negative refractive power in its compressed state so that a subject's eye will have a total negative power on application of a compression force F. In this case, a subject can wear spectacles with positive lenses whereby the subject's eye and his spectacles constitute a Gallilean telescope enabling him to see far objects in a magnified fashion.

Figure 22:
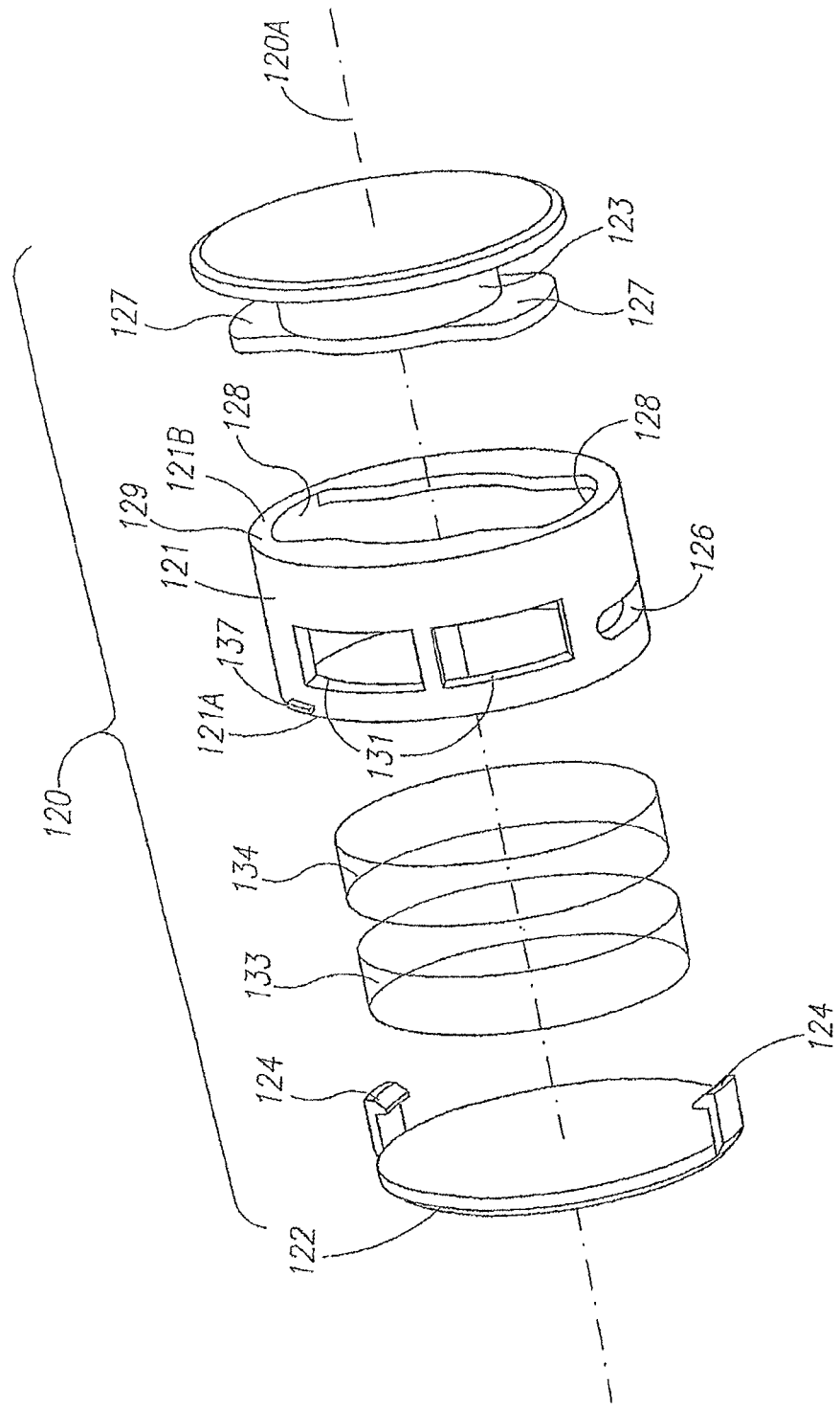
FIG. 22 is an exploded view of a still yet another discrete AIOL for use in a haptics system adapted to be securely fixed in a human eye's annular ciliary sulcus.
Figure 23:
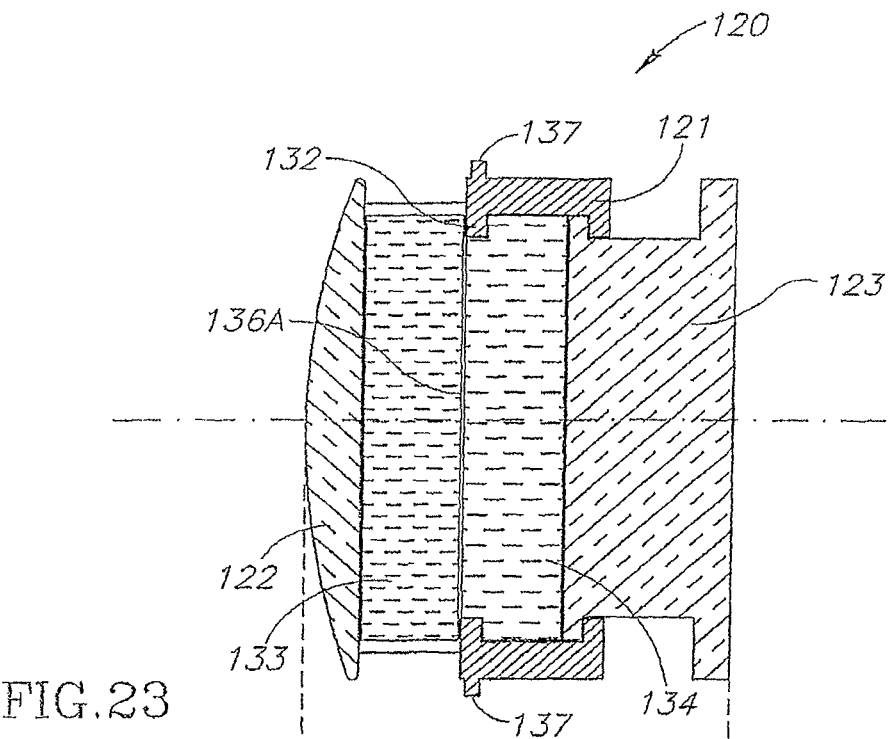
FIG. 23 is a longitudinal cross section view of FIG. 22's AIOL in its non-compressed state.
Figure 24:
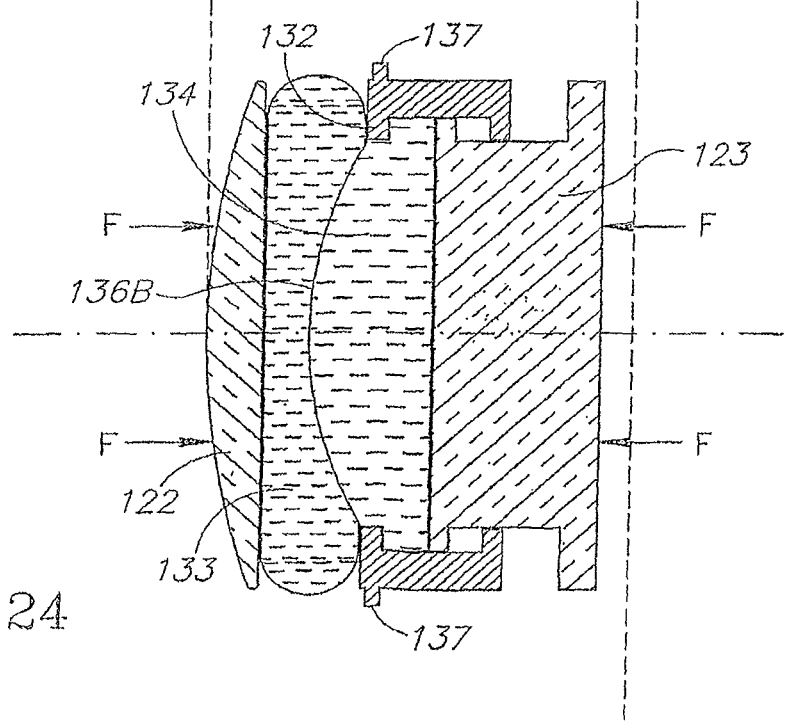
FIG. 24 is a longitudinal cross section view of FIG. 22's AIOL in its compressed state.
Figure 25:
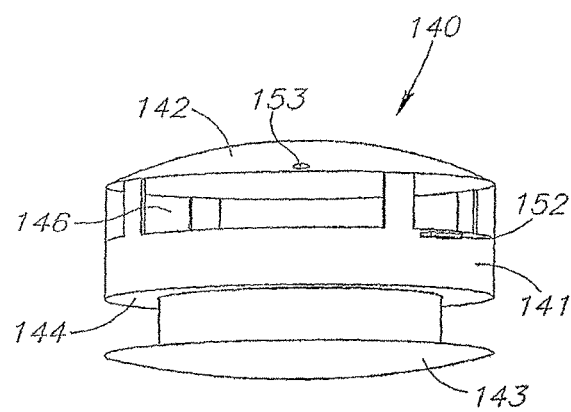
FIG. 25 is a side view of a still yet another discrete AIOL in its non-compressed state for use in a haptics system adapted to be securely fixed in a human eye's annular ciliary sulcus.
Figure 26:
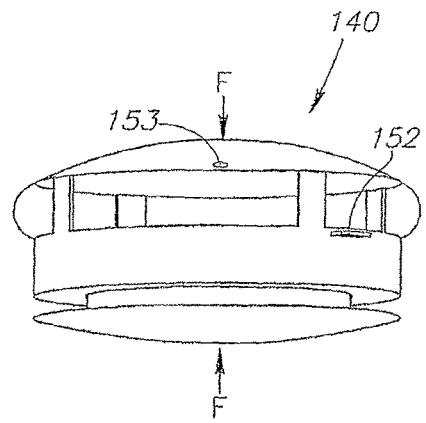
FIG. 26 is a side view of FIG. 25's AIOL in its compressed state.
Figure 27:
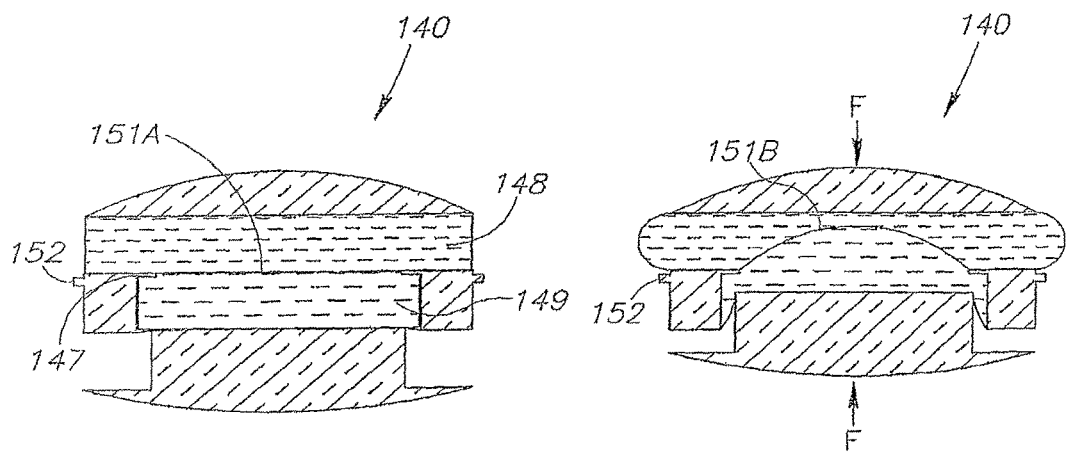
FIG. 27 is a cross section view of FIG. 25's AIOL in its non-compressed state.
Figure 28:
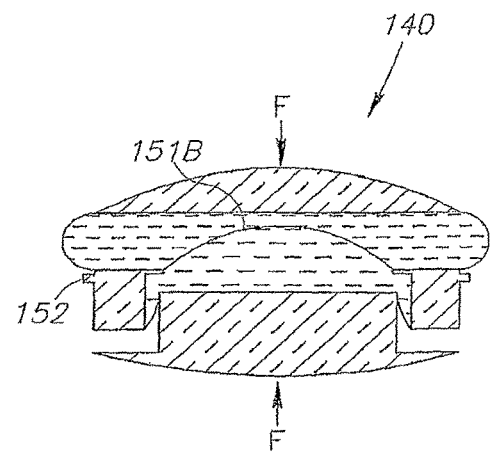
FIG. 28 is a cross section view of FIG. 25's AIOL in its compressed state.

FIGS. 22-24 show a discrete AIOL 120 suitable for use in the haptics system 32 for self-anchoring implantation in a human eye's annular ciliary sulcus. The AIOL 120 has a longitudinal axis 120A intended to be co-direction with a human eye's visual axis, a cylindrical housing 121 having a leading end 121A fitted with an anterior member 122 and a trailing end 121B fitted with a piston 123 reciprocal with respect to the housing 121. The housing 121 is formed from a suitable rigid bio-compatible transparent material, for example, PMMA, and the like. The anterior member 122 is formed with a pair of clamp members 124 for snap fit insertion in a pair of apertures 126 formed in the housing 121. The piston 123 is formed with a pair of keys 127 for insertion in a pair of keyways 128 formed in a trailing surface 129 of the housing 121. Quarter turn rotation of the piston 123 in the housing 121 prevents the piston 123 from being disengaged from the housing 121 but enables reciprocation with respect thereto. The housing 121 is provided with peripheral apertures 131 relative to the longitudinal axis 120A and an annular flange 132 deployed between the trailing surface 129 and the apertures 131 (see FIGS. 23 and 24). Preferably both the anterior member 122 and the piston 123 have positive optical power or alternatively only one of them has positive optical power as in the case of the plano-convex anterior member 122 and the flat piston 123.

The housing 121 houses a pair of shape memory disc-like optical elements 133 and 134 in a similar fashion as the AIOL 91 insofar that the optical elements 133 and 134 have a flat surface 136A in a compressed state of the AIOL 120 (see FIG. 23) and a curved surface 136B in its compressed state (see FIG. 24). FIG. 24 shows the optical element 134 bulging into the optical element 133 which in turn causes the optical element 133 to bulge radially through the apertures 131. In the case that the optical element 133 has a greater refractive index than the optical element 134, the curved surface 136B acts as a concave lens such that the AIOL 120 is suitable for near vision in its non-compressed state (see FIG. 23) and distance vision in its compressed state (see FIG. 24). The leading end 121A is formed with lugs 137 for traveling along the stepped tracks 52. The anterior member 122 is formed with blind manipulation notches 138 (not shown) for selectively receiving the handheld manipulation tool's tip 38A for enabling in situ manipulation of the AIOL 120.

FIGS. 25-28 show a discrete AIOL 140 suitable for use in the haptics system 32 for self-anchoring implantation in a human eye's annular ciliary sulcus. The AIOL 140 is similar in operation to be AIOL 120 but differs therefrom insofar as it is constructed as a single monolithic structure for facilitating insertion into a subject's eye through a relatively small incision. The AIOL 140 includes a housing 141 having an anterior member 142, a piston member 143 joined to the housing 141 by a flexible membrane 144 enabling reciprocation between a non-compressed state and a compressed state, peripheral apertures 146, and an annular flange 147. The housing 141 houses optical elements 148 and 149 which can be injected therein, and which have a flat surface 151A in the non-compressed state of the AIOL 140 (see FIG. 27) and a curved surface 151B in its compressed state (see FIG. 28). In the case that the optical element 148 has a greater refractive index than the optical element 149, the curved surface 151B acts as a concave lens such that the AIOL 140 is suitable for near vision in its non-compressed state (see FIG. 27) and distance vision in its compressed state. (see FIG. 28). The housing 141 is formed with lugs 152 for traveling along the stepped tracks 52. The anterior member 142 is formed with blind manipulation notches 153 for selectively receiving the handheld manipulation tool's tip 38A for enabling in situ manipulation of the AIOL 140.

Figures 29, 30:
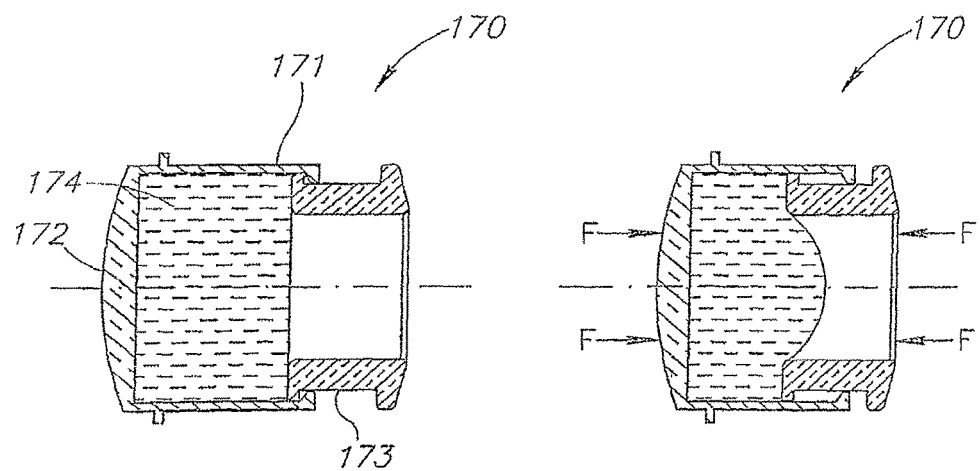
FIG. 29 is longitudinal cross section view of a still yet another discrete AIOL in its non-compressed state for use in a haptics system adapted to be securely fixed in a human eye's annular ciliary sulcus.
FIG. 30 is a longitudinal cross section of FIG. 29's AIOL in its compressed state.

FIGS. 29 and 30 show a discrete AIOL 170 suitable for use in the haptics system 32 for self-anchoring implantation in a human eye's annular ciliary sulcus. The AIOL 170 includes a cup-shaped housing 171 with an anterior member 172 and a trailing tubular piston 173 reciprocal between a most extended position (see FIG. 29) and a most compressed position (see FIG. 30). The housing 171 houses a shape memory optical element 174 resiliently elastically deformable between a non-compressed disc-like shape (see FIG. 29), and a compressed shape bulging into the piston 173 in a posterior direction on application of a compression force F (see FIG. 30). The housing 171 is formed from a suitable rigid bio-compatible material, for example, PMMA, and the like. The optical element 174 is typically constituted by a suitable silicone or water based gel having a refractive index greater than the refractive index of a human eye's aqueous humor such that the AIOL 170 is suitable for distance vision in its non-compressed state (see FIG. 29) and near vision in its compressed state (see FIG. 30).

Figures 31, 32:
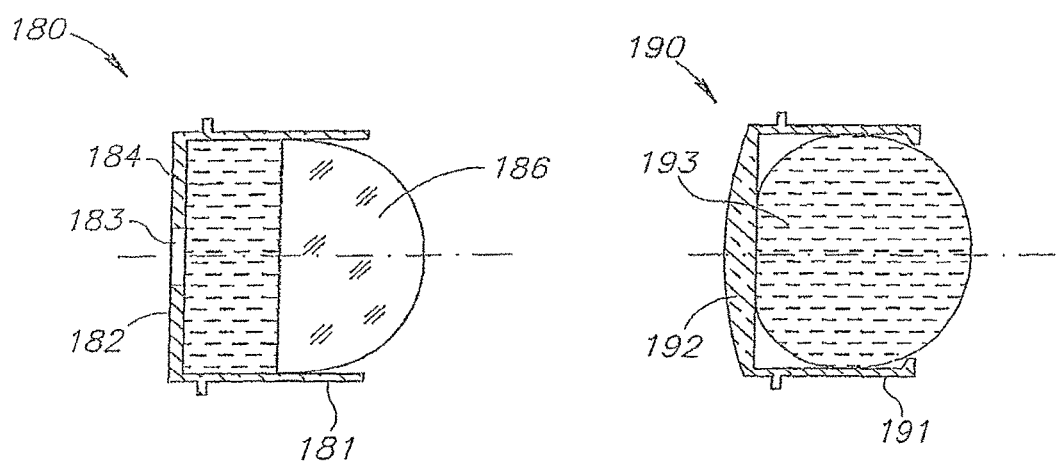
FIG. 31 is a longitudinal cross section of still yet another discrete AIOL in its non-compressed state for use in a haptics system adapted to be securely fixed in a human eye's annular ciliary sulcus.
FIG. 32 is a longitudinal cross section of a still yet another discrete AIOL in its non-compressed state for use in a haptics system adapted to be securely fixed in a human eye's annular ciliary sulcus.

FIG. 31 shows a discrete AIOL 180 suitable for use in the haptics system 32 for self-anchoring implantation in a human eye's annular ciliary sulcus. The AIOL 180 includes a cup-shaped housing 181 with an anterior member 182 having a central aperture 183, a shape memory disc-like optical element 184, and a semi-spherical posterior member 186. The optical element 184 is resiliently elastically deformable between its natural disc-like shape and bulging through the aperture 183 on application of a compression force F. The housing 181 is formed from a suitable rigid bio-compatible material, for example, PMMA, and the like. The optical element 184 is typically constituted by a suitable silicone or water based gel having a refractive index greater than the refractive index of a human eye's aqueous humor whereupon such that the AIOL 180 is suitable for distance vision in its natural state and near vision in its compressed state.

FIG. 32 shows a discrete AIOL 190 suitable for use in a haptics system adapted to be securely fixed in a human eye's annular ciliary sulcus. The AIOL 190 includes a cup-shaped housing 191 with an anterior member 192 and a shape memory spherical optical element 193 resiliently elastically deformable between a natural spherical shape and a flattened shape on application of a compression force F thereagainst in the direction of the anterior member 192. The optical element 193 is typically constituted by a suitable silicone or water based gel having a refractive index greater than the refractive index of a human eye's aqueous humor such that the AIOL 190 is suitable for near vision in its natural state and distance vision in its compressed state.

Figure 33:
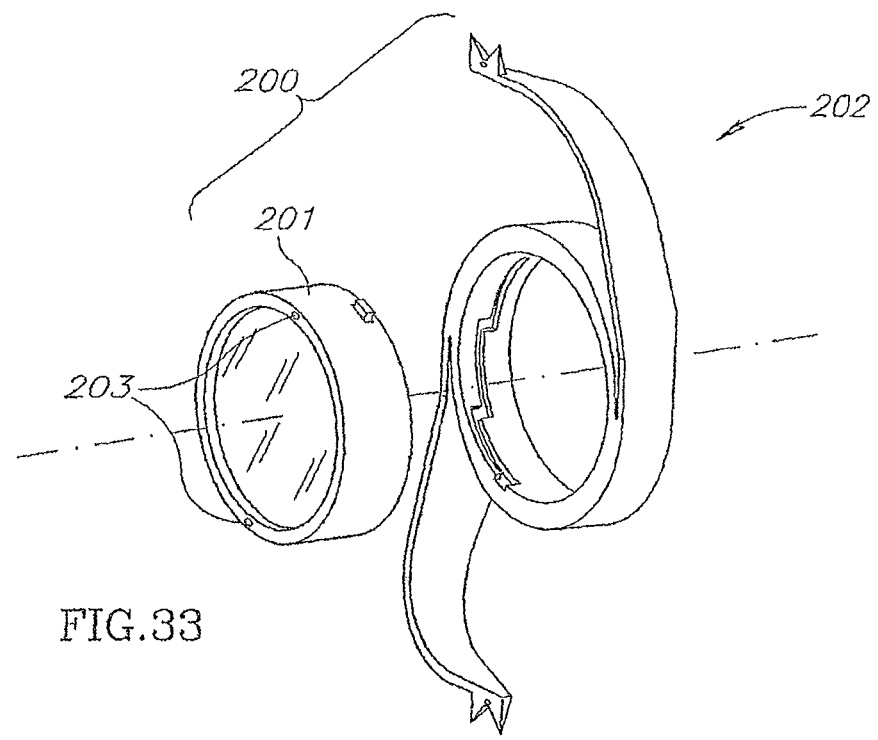
FIG. 33 is a pictorial view of a disassembled "push and twist" AIOL assembly in accordance with another "push and twist" bayonet arrangement.

FIG. 33 shows a "push and twist" AIOL assembly 200 similar in construction and operation to the "push and twist" AIOL assembly 31 but differing therefrom insofar that a discrete AIOL 201 is inserted into a discrete haptics system 202 from an anterior direction as opposed to a posterior direction. In this case, the AIOL 201 is provided with a pair of blind manipulation notches 203 for enabling in situ manipulation by means of a handheld manipulation tool 36.

Figure 34:
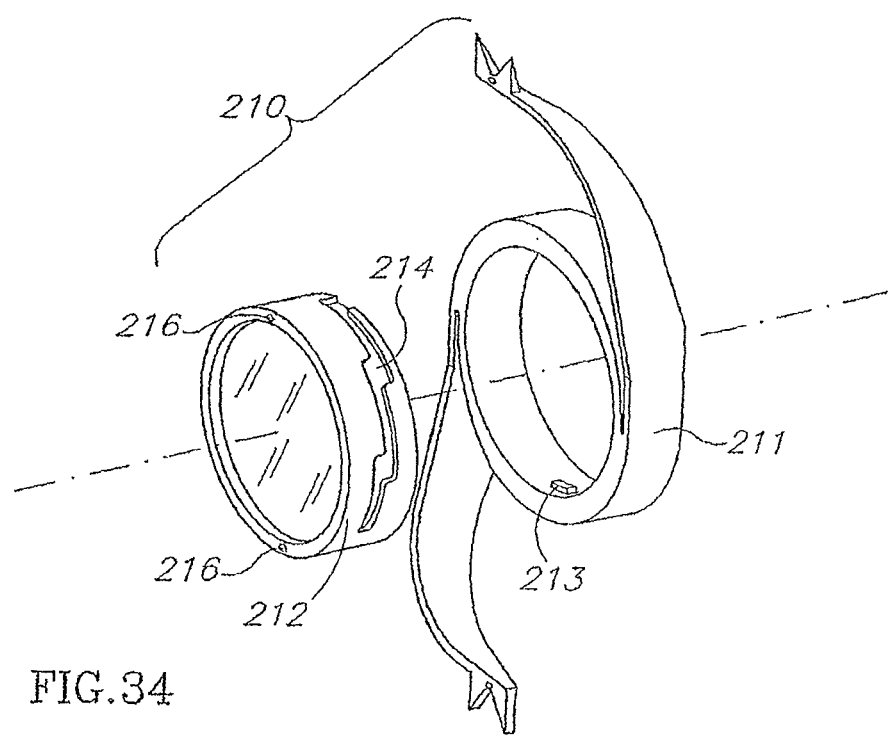
FIG. 34 is a pictorial view of a disassembled "push and twist" AIOL assembly in accordance with yet another "push and twist" bayonet arrangement.

FIG. 34 shows a "push and twist" AIOL assembly 210 similar in construction and operation to the "push and twist" AIOL assembly 31 but differing therefrom insofar that it has a reverse "push and twist" bayonet arrangement with respect to the "push and twist" bayonet arrangement 34. In other words, the AIOL assembly 210 includes a haptics system 211 and an AIOL 212, and the former is provided with lugs 213 and the latter is formed with two or more equidistant stepped tracks 214. The reverse "push and twist" bayonet arrangement is advantageous over the "push and twist" bayonet arrangement 34 insofar that a discrete AIOL can be formed with an axial length L2 which is greater than a main body's axial length L1 for enabling in situ manual selective axial displacement along an adjustment stroke longer than the main body's axial length L1. The AIOL 212 is formed with blind manipulation notches 216 for enabling in situ manipulation by means of a handheld manipulation tool 36. The reverse "push and twist" bayonet arrangement can be implemented with an AIOL 212 inserted into a haptics system 211 from either an anterior direction as shown or a posterior direction similar to the "push and twist" bayonet arrangement 34.

Figure 35:
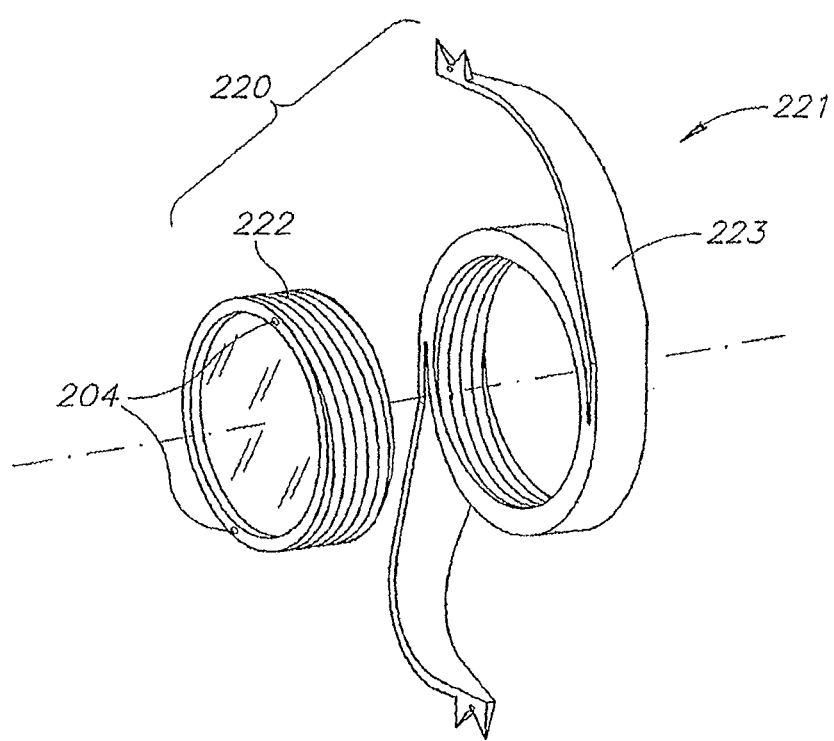
FIG. 35 is a pictorial view of a disassembled AIOL assembly with a screw thread arrangement for enabling in situ manual selective axial displacement of an AIOL along a human eye's visual axis.

FIG. 35 shows an AIOL assembly 220 similar to the AIOL assembly 31 but employing a screw thread arrangement 221 instead of the "push and twist" bayonet arrangement 34 for enabling relative movement of a discrete AIOL 222 with respect to a discrete haptics system 223. The AIOL assembly 220 can also be readily implemented to enable an adjustment stroke along a human eye's visual axis longer than a main body's axial length L1. The AIOL 222 is provided with a pair of blind manipulation notches 224 for enabling in situ manipulation by means of a handheld manipulation tool 36.

While the invention has been described with respect to a limited number of embodiments, it will be appreciated that many variations, modifications, and other applications of the invention can be made within the scope of the appended claims. The discrete AIOLs 120, 140, 170, and 180 can be readily formed as unitary AIOL assemblies similar to the unitary AIOL assemblies 80 and 110.

The invention claimed is:

1. An accommodating intraocular lens (AIOL) system for implantation in a human eye, comprising:
   an accommodating intraocular lens comprising:
      a housing defining, at least in part, a cavity, the housing formed of a first material;
      an optical element contained within the cavity of the housing, the optical element capable of being deformed from a non-bulging state to a bulging state suitable for near vision, wherein the optical element is formed of a second material that is different from the first material, is flowable, and has a refractive index greater than a refractive index of aqueous humor; and
      a piston reciprocally movable relative to the housing between an extended position and a compressed position, wherein the piston is adapted to be responsive to ciliary muscle contraction,
      wherein application of a compression force on the optical element by the piston at a first location causes the optical element to bulge at a second location away from the first location to create the bulging state of the optical element; and
   a self-anchoring haptics system extending in a plane perpendicular to a visual axis of the accommodating intraocular lens, the self-anchoring haptics system adapted to engage with ocular tissue to form at least two spaced-apart, stationary anchor points for retaining the accommodating intraocular lens in the eye.

2. The AIOL system according to claim 1, wherein the self-anchoring haptics system is integrally formed with the accommodating intraocular lens.

3. The AIOL system according to claim 1, wherein the housing has a diameter of at least 6 mm to about 7 mm.

4. The AIOL system according to claim 1, wherein the housing is formed of a silicone or acrylic based polymer material.

5. The AIOL system according to claim 1, wherein the self-anchoring haptics system includes a pair of C-shaped haptics extending from the accommodating intraocular lens in opposite directions.

6. The AIOL system according to claim 1, wherein the self-anchoring haptics system includes spaced apart pointed puncturing members.

7. The AIOL system according to claim 1, wherein the optical element has a continuous, slightly curvilinear leading surface in the non-bulging state.

8. The AIOL system according to claim 1, wherein the accommodating intraocular lens has a continuously variable Diopter strength from a minimum Diopter strength suitable for distance vision and a maximum Diopter strength suitable for near vision.

9. The AIOL system according to claim 1, wherein the optical element is suitable for distance vision in the non-bulging state and near vision in the bulging state.

10. The AIOL system according to claim 1, wherein the optical element is formed of a silicone-based material.

\* \* \* \* \*